United States Patent
Lanza et al.

(10) Patent No.: US 9,468,607 B2
(45) Date of Patent: Oct. 18, 2016

(54) LIGAND DIRECTED TOROIDAL NANOPARTICLES FOR THERAPY AND DIAGNOSTIC IMAGING

(75) Inventors: Gregory M. Lanza, St. Louis, MO (US); Samuel A. Wickline, St. Louis, MO (US); Dipanjan Pan, St. Louis, MO (US)

(73) Assignee: WASHINGTON UNIVERSITY, St. Louis, MO (US)

( * ) Notice: Subject to any disclaimer, the term of this patent is extended or adjusted under 35 U.S.C. 154(b) by 1189 days.

(21) Appl. No.: 12/682,098

(22) PCT Filed: Oct. 9, 2008

(86) PCT No.: PCT/US2008/079414
§ 371 (c)(1),
(2), (4) Date: Aug. 12, 2010

(87) PCT Pub. No.: WO2009/049089
PCT Pub. Date: Apr. 16, 2009

(65) Prior Publication Data
US 2010/0297007 A1    Nov. 25, 2010

Related U.S. Application Data

(60) Provisional application No. 60/978,679, filed on Oct. 9, 2007.

(51) Int. Cl.
| *A61K 9/107* | (2006.01) |
| *A61K 9/51* | (2006.01) |
| *B82Y 5/00* | (2011.01) |
| *A61K 49/18* | (2006.01) |

(52) U.S. Cl.
CPC ........... *A61K 9/5146* (2013.01); *A61K 9/1075* (2013.01); *A61K 49/1824* (2013.01); *B82Y 5/00* (2013.01); *Y10T 428/2985* (2015.01)

(58) Field of Classification Search
None
See application file for complete search history.

(56) References Cited

U.S. PATENT DOCUMENTS

| 3,215,572 | A | 11/1965 | Papell |
| 4,297,623 | A | 10/1981 | Dupont |
| 5,077,036 | A | 12/1991 | Long, Jr. |
| 5,114,703 | A | 5/1992 | Wolf et al. |
| 5,171,755 | A | 12/1992 | Kaufman et al. |
| 5,260,306 | A * | 11/1993 | Boardman et al. ........... 514/291 |
| 5,304,325 | A | 4/1994 | Kaufman et al. |
| 5,350,571 | A | 9/1994 | Kaufman et al. |
| 5,393,524 | A | 2/1995 | Quay |
| 5,403,575 | A | 4/1995 | Kaufman et al. |
| 5,534,499 | A | 7/1996 | Ansell |
| 5,690,907 | A | 11/1997 | Lanza et al. |
| 5,780,010 | A | 7/1998 | Lanza et al. |
| 5,820,848 | A | 10/1998 | Boni et al. |
| 5,958,371 | A | 9/1999 | Lanza et al. |
| 5,989,520 | A | 11/1999 | Lanza et al. |
| 6,368,586 | B1 | 4/2002 | Jacob et al. |
| 6,413,544 | B1 * | 7/2002 | Smyth-Templeton et al. .............. 424/450 |
| 6,491,903 | B1 | 12/2002 | Forster |
| 6,579,846 | B1 * | 6/2003 | Zirnstein et al. ............. 510/499 |
| 7,022,313 | B2 * | 4/2006 | O'Connor et al. ............. 424/48 |
| 2002/0034536 | A1 | 3/2002 | Perkins et al. |
| 2003/0157179 | A1 | 8/2003 | Blum et al. |
| 2003/0185879 | A1 | 10/2003 | Boulikas |
| 2004/0142474 | A1 * | 7/2004 | Mahato et al. ............... 435/458 |
| 2004/0229945 | A1 | 11/2004 | Satchi-Fainaro et al. |
| 2005/0037050 | A1 * | 2/2005 | Weber ........................... 424/426 |
| 2005/0079131 | A1 | 4/2005 | Lanza et al. |
| 2005/0095267 | A1 | 5/2005 | Campbell et al. |
| 2006/0008461 | A1 | 1/2006 | Yatvin et al. |
| 2006/0015261 | A1 | 1/2006 | Mann et al. |
| 2006/0159619 | A1 | 7/2006 | Becker |
| 2006/0228299 | A1 | 10/2006 | Thorpe et al. |
| 2006/0264397 | A1 | 11/2006 | Kucera et al. |
| 2007/0020308 | A1 | 1/2007 | Richard et al. |
| 2007/0110777 | A1 | 5/2007 | Joabsson |
| 2007/0154539 | A1 | 7/2007 | Fountain |
| 2008/0269875 | A1 | 10/2008 | Zhao |
| 2008/0286321 | A1 | 11/2008 | Reneker et al. |
| 2008/0286372 | A1 * | 11/2008 | Pacetti et al. ................. 424/493 |
| 2009/0148383 | A1 | 6/2009 | Peter |
| 2009/0163437 | A1 | 6/2009 | Rusconi |
| 2009/0202429 | A1 | 8/2009 | Diacovo et al. |
| 2009/0208548 | A1 | 8/2009 | Mason et al. |
| 2010/0028994 | A1 * | 2/2010 | DeSimone et al. ........... 435/325 |
| 2010/0297019 | A1 | 11/2010 | Lanza et al. |

(Continued)

FOREIGN PATENT DOCUMENTS

| WO | 96/20698 | A2 | 7/1996 |
| WO | 01/74337 | A1 | 10/2001 |

(Continued)

OTHER PUBLICATIONS

Su, Y., "Assembly of polydiacetylene vesicles on solid substrates", 2005, J. Colloid and Interface Science, 292, pp. 271-276.*
Brownlie A., et al., "PEI-based vesicle-polymer hybrid gene delivery system with improved biocompatibility", 2004, Int. J. Pharmaceutics, 274, pp. 41-52.*
Forrest, M.L., et al., "Partial Acetylation of Polyethylenimine Enhances In Vitro Gene Delivery", 2004, Pharmaceutical Research, pp. 365-371.*
International Search Report and Written Opinion from related International Application No. PCT/US2008/079414, Dec. 15, 2008.
International Search Report and Written Opinion dated Dec. 15, 2008 from related International application No. PCT/US08/079414, 14 pgs.

(Continued)

*Primary Examiner* — Michael G Hartley
*Assistant Examiner* — Lance Rider
(74) *Attorney, Agent, or Firm* — Polsinelli PC

(57) ABSTRACT

The present invention provides nanoparticles, methods of making the nanoparticles, and methods of using the nanoparticles to deliver therapeutic agents and/or imaging agents.

20 Claims, 23 Drawing Sheets
(20 of 23 Drawing Sheet(s) Filed in Color)

(56) References Cited

U.S. PATENT DOCUMENTS

| | | |
|---|---|---|
| 2013/0064765 A1 | 3/2013 | Myerson et al. |
| 2013/0122100 A1 | 5/2013 | Lanza et al. |

FOREIGN PATENT DOCUMENTS

| | | |
|---|---|---|
| WO | 03/015831 A1 | 2/2003 |
| WO | 2004/017907 A2 | 3/2004 |
| WO | 2005/014051 A1 | 2/2005 |
| WO | 2006/072943 A2 | 7/2006 |
| WO | 2006/117720 A2 | 11/2006 |
| WO | 2007/034359 A2 | 3/2007 |
| WO | 2007/106683 A2 | 9/2007 |
| WO | 2008/063157 A2 | 5/2008 |
| WO | 2008/109712 A2 | 9/2008 |
| WO | 2009/049083 A1 | 4/2009 |
| WO | 2009/049089 A1 | 4/2009 |
| WO | 2011/084700 A1 | 7/2011 |
| WO | 2011/130674 A1 | 10/2011 |
| WO | 2011/133635 A2 | 10/2011 |
| WO | 2014/179793 A1 | 11/2014 |

OTHER PUBLICATIONS

Kleemann, Modified polyethylenimines as non-viral gene delivery systems for aerosol gene therapy: investigations of the complex structure and statbility during air-jet and ultrasonic nebulization, Journal of Controlled Release, 2004, pp. 437-450, vol. 100.

Acharyya et al., "Interplay of IKK/NF-κB signaling in macrophages and myofibers promotes muscle degeneration in Duchenne muscular dystrophy", The Journal of Clinical Investigation, 2007, pp. 889-901, vol. 117, No. 4.

Ambrose et al., "Angiographic Progression of Coronary Artery Disease and the Development of Myocardial Infarction", JACC, 1988, pp. 56-62, vol. 12, No. 1.

Andersson et al., "Heparin cofactor II activity in plasma: Application of an automated assay method to the study of a normal adult population", Scandinavian Journal of Haematology, 1986, pp. 96-102, vol. 36.

Angelova et al., "Liposome Electroformation", Faraday Discuss. Chem. Soc., 1986, pp. 303-311, vol. 81.

Ansell et al., "The Pharmacology and Management of the Vitamin K Antagonists", CHEST, 2004, pp. 204S-233S, vol. 126, No. 3.

Bacia et al., "Fluorescence Correlation Spectroscopy", Methods in Molecular Biology, 2007, pp. 73-84, vol. 398.

Baud et al., "Is NF-κB a good target for cancer therapy? Hopes and pitfalls", Nat Rev Drug Discov., 2009, pp. 33-40, vol. 8, No. 1.

Benson, "The Present Status of Coronary Arterial Disease", Archives of Pathology & Laboratory Medicine, 1926, pp. 876-916, vol. 2.

Bernal-Mizrachi et al., "The role of NF-κB-1 and NF-κB-2-mediated resistance to apoptosis in lymphomas", PNAS, 2006, pp. 9220-9225, vol. 103, No. 24.

Bertina et al., "Hereditary Heparin Cofactor II Deficiency and the Risk of Development of Thrombosis", Journal of Thrombosis and Haemostasis, 1987, pp. 196-200, vol. 57, No. 2.

Bhoj et al., "Ubiquitylation in innate and adaptive immunity", Nature, 2009, pp. 430-437, vol. 458.

Bibette, "Monodisperse ferrofluid emulsions", Journal of Magnetism and Magnetic Materials, 1993, pp. 37-41, vol. 122.

Bidwell III et al., "Therapeutic peptides for cancer therapy. Part I—peptide inhibitors of signal transduction cascades", Expert Opin. Drug Deliv., 2009, pp. 1033-1047, vol. 6, No. 10.

Bode et al., "The refined 1.9 Å crystal structure of a human α-thrombin: interaction with D-Phe-Pro-Arg chloromethylketone and significance of tye tyr-Pro-Pro-Trp insertion segment", The EMBO Journal, 1989, pp. 3467-3475, vol. 8, No. 11.

Bode et al., "The refined 1.9-Å X-ray crystal structure of D-Phe-Pro-Arg chloromethylketone-inhibited human α-thrombin: Structure analysis, overall structure, electrostatic properties, detailed active-site geometry, and structure-function relationships", Protein Science, 1992, pp. 426-471, vol. 1.

Bousser, "Antithrombotic Agents in the Prevention of Ischemic Stroke", Cerebrovascular Diseases, 2009, pp. 12-19, vol. 27 (suppl 3).

Bowen, "Particle Size Distribution Measurement from Millimeters to Nanometers and from Rods to Platelets", Journal of Dispersion Science and Technology, 2002, pp. 631-662, vol. 23, No. 5.

Boxus et al., "The HTLV-I Tax interactome", Retrovirology, 2008, pp. 76-99, vol. 5.

Bretschneider et al., "Evidence for functionally active protease-activated receptor-4 (PAR-4) in human vascular smooth muscle cells", British Journal of Pharmacology, 2001, pp. 1441-1446, vol. 132, No. 7.

Bretschneider et al., "Evidence for functionally active protease-activated receptor-3 (PAR-3) in human vascular smooth muscle cells", Journal of Thrombosis and Haemostasis, 2003, pp. 704-709, vol. 90.

Brown et al., "Incomplete lysis of thrombus in the moderate underlying atherosclerotic lesion during intracoronary infusion of streptokinase for acute myocardial infarction: quantitative angiographic obser-vations", Circulation, 1986, pp. 653-661, vol. 73, No. 4.

Caruthers et al., "Anti-angiogenic perfluorocarbon nanoparticles for diagnosis and treatment of atherosclerosis", WIREs Nanomedicine and Nanobiotechnology, 2009, pp. 311-323, vol. 1.

Casscells et al., "Thermal detection of cellular infiltrates in living atherosclerotic plaques: possible implications for plaque rupture and thrombosis", The Lancet, 1996, pp. 1447-1449, vol. 347.

Cerqueira, "Current Status of Radionuclide Tracer Imaging of Thrombi and Atheroma", Seminars in Nuclear Medicine, 1999, pp. 339-351, vol. 29, No. 4.

Charles, "Some Applications of Magnetic Fluids—Use as an Ink and In Microwave Systems"Journal of Magnetism and Magnetic Materials, 1987, pp. 50-358, vol. 65.

Cho et al., "Ability of Surfactant Micelles to Alter the Physical Location and Reactivity of Iron in Oil-in-Water Emulsion", Journal of Agricultural and Food Chemistry, 2002, pp. 5704-5710, vol. 50, No. 20.

Collen et al., "In vivo studies of a synthetic inhibitor of thrombin", J. Lab. Clin. Med., 1982, pp. 76-83, vol. 99, No. 1.

Constantinides, "Plaque Fissures in Human Coronary Thrombosis", Journal of Atherosclerosis Research, 1966, pp. 1-17, vol. 6.

Coughlin, "Thrombin signalling and protease-activated receptors", Nature, 2000, pp. 258-264, vol. 407.

Davies, "Anatomic Features in Victims of Sudden Coronary Death, Coronary Artery Pathology", Circulation, Supplement I, 1992, pp. I19-I24, vol. 85, No. 1.

Davies et al., "The effect of temperature and oleate adsorption on the growth of maghemite particles", Journal of Magnetism and Magnetic Materials, 1993, pp. 24-28, vol. 122.

de Korte et al., "Characterization of plaque components and vulnerability with intravascular ultrasound elastography", Phys. Med. Biol., 2000, pp. 1465-1475, vol. 45.

Deng et al., "Magnetic and conducting $Fe_3O_4$—cross-linked polyaniline nanoparticles with core-shell structure", Polymer, 2002, pp. 2179-2184, vol. 43.

Deng et al., "Preparation of magnetic polymeric particles via inverse microemulsion polymerization process", Journal of Magnetism and Magnetic Materials, 2003, pp. 69-78, vol. 257.

Di Cera, "Thrombin", Mol Aspects Med., 2008, pp. 203-254, vol. 29, No. 4.

Dresco et al., "Preparation and Properties of Magnetite and Polymer Magnetite Nanoparticles", Langmuir, 1999, pp. 1945-1951, vol. 15, No. 6.

Dubertret et al., "In Vivo Imaging of Quantum Dots Encapsulated in Phospholipid Micelles", Science, 2002, pp. 1759-1762, vol. 298.

Duguid, "Thrombosis As a Factor in the Pathogenesis of Coronary Atherosclerosis", J Path Bact., 1946, pp. 207-212, vol. 58.

Duguid, "Thrombosis as a Factor in the Pathogenesis of Aortic Atherosclerosis", J Path Bact., 1948, pp. 57-61, vol. 60.

Extended European Search report from related European Patent Application No. EP 10 84 2655, dated May 27, 2015; 12 pgs.

(56) References Cited

OTHER PUBLICATIONS

Extended European Search report from related European Patent Application No. EP 11769698.9, dated May 6, 2014; 3 pgs.
Extended European Search Report from related European Patent Application No. EP 08 83 7973, dated Jan. 2, 2014; 9 pgs.
Fareed et al., "Changing trends in anti-coagulant therapies. Are heparins and oral anti-coagulants challenged?", International Journal of Angiology, 2008, pp. 176-192, vol. 27, No. 3.
Feltin et al., "New Technique for Synthesizing Iron Ferrite Magnetic Nanosized Particles", Langmuir, 1997, pp. 3927-3933, vol. 13, No. 15.
Flacke et al., "Novel MRI Contrast Agent for Molecular Imaging of Fibrin: Implications for Detecting Vulnerable Plaques", Circulation, 2001, pp. 1280-1285, vol. 104.
Flaim, "Pharmacokinetics and Side Effects of Perfluorocarbon-Based Blood Substitutes", Artificial Cells, Blood Substitutes, and Immobilization Biotechnology, 1994, pp. 1043-1054, vol. 22, No. 4.
Furie et al., "Mehanisms of Thrombus Formation", The New England Journal of Medicine, 2008, pp. 938-949, vol. 359, No. 9.
Garg et al., "Nuclear transcription factor-κB as a target for cancer drug development", Leukemia, 2002, pp. 1053-1068, vol. 16.
Ghigliotti et al., "Prolonged Activation of Prothrombin on the Vascular Wall After Arterial Injury", Arteriosclerosis, Thrombosis, and Vascular Biology, 1998, pp. 250-257, vol. 18.
Gilchrist et al., "Selective Inductive Heating of Lymph Nodes", Annals of Surgery, 1957, pp. 596-606, vol. 146, No. 4.
Glagov et al., "Compensatory Enlargement of Human Atherosclerotic Coronary Arteries", The New England Journal of Medicine, 1987, pp. 1371-1375, vol. 316, No. 22.
Gross et al., "New Antithrombotic Drugs", Clinical Pharmacology & Therapeutics, 2009, pp. 139-146, vol. 86, No. 2.
Grossman et al., "Development of leukemia in mice transgenic for the tax gene of human T-cell leukemia virus type I", Proc. Natl. Acad. Sci. USA, 1995, pp. 1057-1061, vol. 92.
Grossman et al., "Cytokine Expression and Tumorigenicity of Large Granular Lymphocytic Leukemia Cells From Mice Transgenic for the tax Gene of Human T-Cell Leukemia Virus Type I", Blood, 1997, pp. 783-794, vol. 90, No. 2.
Hess et al., "Biological and Chemical Applications of Fluorescence Correlation Spectroscopy: A Review", Bochemistry, 2002, pp. 697-705, vol. 41, No. 3.
Hirano, "The Roles of Proteinase-Activated Receptors in the Vascular Physiology and Pathophysiology", Arteriosclerosis, Thrombosis, and Vascular Biology, 2007, pp. 27-36, vol. 27.
Hirsh et al., "Beyond Unfractionated Heparin and Warfarin: Current and Future Advances", Circulation, 2007, pp. 552-560, vol. 116.
Hofman et al., "Quantification of In-Plane Motion of the Coronary Arteries During the Cardiac Cycle: Implications for Acquisition Window Duration for MR Flow Quantification", Journal of Magnetic Resonance Imaging, 1998, pp. 568-576, vol. 8, No. 3.
Hu et al., "Imaging of Vx-2 rabbit tumors with αvβ3-integrin-targeted 111In nanoparticles", International Journal of Cancer, 2007, pp. 1951-1957, vol. 120.
International Search Report and Written Opinion from related International Application No. PCT/US2014/36762, dated Oct. 9, 2014; 7 pgs.
International Search Report and Written Opinion from related International Application No. PCT/US2011/32744, dated Jul. 8, 2011; 10 pgs.
International Search Report and Written Opinion from related International Application No. PCT/US2010/61103, dated Apr. 6, 2011; 12 pgs.
International Search Report and Written Opinion from related International Application No. PCT/US2008179404, dated Dec. 24, 2008; 8 pgs.
Ivey et al., "Thrombin regulates vascular smooth muscle cell proteoglycan synthesis via PAR-1 and multiple downstream signalling pathways", Thrombosis Research, 2008, pp. 288-297, vol. 123.

Kaiser et al., "Pharmacology of Synthetic Thrombin Inhibitors of the Tripeptide Type", Cardiovascular Drug Reviews, 1992, pp. 71-87, vol. 10, No. 1.
Kaneda et al., "Perfluorocarbon Nanoemulsions for Quantitative Molecular Imaging and Targeted Therapeutics", Ann Biomed Eng., 2009, pp. 1922-1933, vol. 37, No. 10.
Karin, "The Beginning of the End: IκB Kinase (IKK) and NF-κB Activation*", The Journal of Biological Chemistry, 1999, pp. 27339-27342, vol. 274, No. 39.
Karin et al., "NF-κB in Cancer: From Innocent Bystander to Major Culprit", Nature Reviews/Cancer, 2002, pp. 301-310, vol. 2.
Karin, "Nuclear factor-κB in cancer development and progression", Nature, 2006, pp. 431-436, vol. 441.
Kettner et al., "D-Phe-Pro-ArgCH2C1-A Selective Affinity Label for Thrombin", Thrombosis Research, 1979, pp. 969-973, vol. 14, No. 6.
Kim et al., "Development of a novel dosage form for intramuscular injection of titrated extract of Centella asiatica in a mixed micellar system", International Journal of Pharmaceutics, 2001, pp. 141-147, vol. 220.
Klocek et al., "Thermodynamics of Melittin Binding to Lipid Bilayers. Aggregation and Pore Formation", Biochemistry, 2009, pp. 2586-2596, vol. 48, No. 12.
Kukrejaet al., "The future of drug-eluting stents", Pharmacological Research, 2008, pp. 171-180, vol. 57.
landfester et al., "Encapsulated magnetite particles for biomedical application", Journal of Physics: Condensed Matter, 2003, pp. S1345-S1361, vol. 15.
Lanza et al., "Molecular Imaging of Stretch-Induced Tissue Factor Expression in Carotid Arteries with Intravascular Ultrasound", Investigative Radiology, 2000, pp. 227-234, vol. 35, No. 4.
Lanza et al., "Targeted Antiproliferative Drug Delivery to Vascular Smooth Muscle Cells With a Magnetic Resonance Imaging Nanoparticle Contrast Agent: Implications for Rational Therapy of Restenosis", Circulation, 2002, pp. 2842-2847, vol. 106.
Lanza et al., "Nanomedicine opportunities for cardiovascular disease with perfluorocarbon nanoparticles", Nanomedicine, 2006, pp. 321-329, vol. 1, No. 3.
Lee, "Anticoagulants in Coronary Artery Disease", Clinical Cardiology, 2008, pp. 615-628, vol. 26.
Liu et al., "Surface Modification and Characterization of Magnetic Polymer Nanospheres Prepared by Miniemulsion Polymerization", Langmuir, 2004, pp. 10278-10282, vol. 20, No. 23.
Liu et al., "Preparation and characterization of biodegradable magnetic carriers by single emulsion-solvent evaporation", Journal of Magnetism and Magnetic Materials, 2007, pp. 84-87, vol. 311.
Lopez-Guerra et al., "NF-κB as a therapeutic target in chronic lymphocytic leukemia", Expert Opin. Ther. Targets, 2010, pp. 275-288, vol. 14, No. 3.
Maclean et al., "Hereditary and Acquired Antithrombin Deficiency: Epidemiology, Pathogenesis and Treatment options", Drugs, 2007, pp. 1429-1440, vol. 67, No. 10.
Mandal et al., "Encapsulation of Magnetic and Fluorescent Nanoparticles in Emulsion Droplets", Langmuir, 2005, pp. 4175-4179, vol. 21, No. 9.
Marsh et al., "Molecular imaging with targeted perfluorocarbon nanoparticles: Quantification of the concentration dependence of contrast enhancement for binding to sparse cellular epitopes", Ultrasound Med Biol., 2007, pp. 950-958, vol. 33, No. 6.
May et al., "Selective Inhibition of NF-κB Activation by a Peptide That Blocks the Interaction of NEMO with the IκB Kinase Complex", Science, 2000, pp. 1550-1554, vol. 289.
May et al., "Individualized antithrombotic therapy in high risk patients after coronary stenting. A double-edged sword between thrombosis and bleeding", Journal of Thrombosis and Haemostasis, 2008, pp. 487-493, vol. 99.
Montagne et al., "Preparation and characterization of narrow sized (o/w) magnetic emulsion", Journal of Magnetism and Magnetic Materials, 2002, pp. 302-312, vol. 250.
Moody et al., "Direct magnetic resonance imaging of carotid artery thrombus in acute stroke", The Lancet, 1999, pp. 122-123, vol. 353.

(56) References Cited

OTHER PUBLICATIONS

Morales et al., "Contrast agents for MRI based on iron oxide nanoparticles prepared by laser pyrolysis", Journal of Magnetism and Magnetic Materials, 2003, pp. 102-109, vol. 266.
Morawski et al., "Quantitative "Magnetic Resonance Immunohistochemistry" with Ligand-Targeted 19F Nanoparticles", Magnetic Resonance in Medicine, 2004, pp. 1255-1262, vol. 52.
Mulder et al., "MR molecular imaging and fluorescence microscopy for identification of activated tumor endothelium using a bimodal lipidic nanoparticle", The FASEB Journal, 2005, pp. 2008-2010, vol. 19.
Mulder et al., "Lipid-based nanoparticles for contrast-enhanced MRI and molecular imaging", NMR in Biomedicine, 2006, pp. 142-164, vol. 19.
Myerson et al., "'Thrombin sponge': A potent nanoparticle approach to inhibiting coagulation in acute thrombosis", The FASEB Journal, 2010, p. 574.2, vol. 24, No. 1.
Myerson et al., "Thrombin-inhibiting perfluorocarbon nanoparticles provide a novel strategy for treatment and magnetic resonance imaging of acute thrombosis", Journal of Thrombosis and Haemostasis, 2011, pp. 1292-1300, vol. 9, No. 7.
Office Action from related U.S. Appl. No. 13/641,252, dated Sep. 30, 2015; 20 pgs.
Office Action from related U.S. Appl. No. 13/641,252, dated Jun. 26, 2015; 11 pgs.
Office Action from related U.S. Appl. No. 13/516,528, dated Sep. 14, 2015; 11 pgs.
Office Action from related U.S. Appl. No. 13/516,528, dated Dec. 9, 2014; 6 pgs.
Office Action from related U.S. Appl. No. 13/516,528, dated May 27, 2014; 7 pgs.
Office Action from related U.S. Appl. No. 13/516,528 dated Oct. 23, 2013; 20 pgs.
Office Action from related U.S. Appl. No. 12/682,094, dated Jan. 14, 2013; 16 pgs.
Office Action from related U.S. Appl. No. 12/682,094, dated May 7, 2012; 15 pgs.
Office Action from related Japanese Patent Application No. 2013-505192, dated Jan. 15, 2015; 2 pgs.
Fourth Office Action from related Chinese Patent Application No. 200880117661.5, dated Jul. 25, 2013; 13 pgs.
Third Office Action from related Chinese Patent Application No. 200880117661.5, dated Jan. 7, 2013; 13 pgs.
Second Office Action from related Chinese Patent Application No. 200880117661.5, dated Jun. 4, 2012; 17 pgs.
First Office Action from related Chinese Patent Application No. 200880117661.5, dated Jul. 20, 2011; 11 pgs.
Pan, et al., "Water Soluble Nano-Bialys: Preparation of a Vascularly Constrained, Slow Releasing Nano-Carrier for Hydrophilic and Hydrophobic Drugs", Oct. 2007, Abstract for presentation in American Chemical Society, Western Regional Meeting 2007, Frontiers in Chemistry, Biopharmaceuticals & Biotechnology.
Pan et al., "Lipid membrane editing with peptide cargo linkers in cells and synthetic nanostructures", The FASEB Journal, 2010, pp. 2928-2937, vol. 24, No. 8.
Pan et al., "Anti-Angiogenesis Therapy in the Vx2 Rabbit Cancer Model with Lipase-cleavable Sn 2 Taxane Phospholipid Prodrug using $\alpha v\beta 3$-Targeted Theranostic Nanoparticles", Theranostics, 2014, pp. 565-578, vol. 4, No. 6.
Partlow et al., "19F magnetic resonance imaging for stem/progenitor cell tracking with multiple unique perfluorocarbon nanobeacons", The FASEB Journal, 2007, pp. 1647-1654, vol. 21.
Pasparakis, "Regulation of tissue homeostasis by NF-κB signalling: implications for inflammatory diseases", Nature Reviews/Immunology, 2009, pp. 778-788, vol. 9.
Peters et al., "Targeting atherosclerosis by using modular, multifunctional micelles", PNAS, 2009, pp. 9815-9819, vol. 106, No. 24.
Petrasek et al., "Precise Measurement of Diffusion Coefficients using Scanning Fluorescence Correlation Spectroscopy", Biophysical Journal, 2008, pp. 1437-1448, vol. 94, No. 4.
Piras et al., "Polymeric nanoparticles for hemoglobin-based oxygen carriers", Biochimica et Biophysica Acta, 2008, pp. 1454-1461, vol. 1784.
Qiu et al., "Novel, Fluorescent, Magnetic, Polysaccharide-Based Microsphere for Orientation, Tracing, and Anticoagulation: Preparation and Characterization", Biomacromolecules, 2005, pp. 1041-1047, vol. 6, No. 2.
Raj et al., "Commercial Applications of Ferrofluids", Journal of Magnetism and Magnetic Materials, 1990, pp. 233-245, vol. 85.
Rhoades et al., "Quantification of α-Synuclein Binding to Lipid Vesicles Using Fluorescence Correlation Spectroscopy", Biophysical Journal, 2006, pp. 4692-4700, vol. 90, No. 12.
Roath, "Biological and biomedical aspects of magnetic fluid technology", Journal of Magnetism and Magnetic Materials, 1993, pp. 329-334, vol. 122.
Roger et al., "Some biomedical applications of ferrofluids", The European Physical Journal Applied Physics, 1999, pp. 321-325, vol. 5.
Rosensweig, "Magnetic Fluids: Tiny ferromagnetic particles suspended in an organic liquid form a new kind of fluid responsive to magnetic fields in queer but useful ways", International Science and Technology, 1966, pp. 48-56.
Rothwarf et al., "IKK-γ is an essential regulatory subunit of the IκB kinase complex", Nature, 1998, pp. 297-300, vol. 395.
Schwartz et al., "Microemboli and Microvascular Obstruction in Acute Coronary Thrombosis and Sudden Coronary Death", Journal of the American College of Cardiology, 2009, pp. 2167-2173, vol. 54, No. 23.
Sie et al., "Constitutional Heparin Co-Factor II Deficiency Associated with Recurrent Thrombosis", The LANCET, 1985, pp. 414-416, vol. 2.
Smale, "Selective Transcription in Response to an Inflammatory Stimulus", Cell, 2010, pp. 833-844, vol. 140, No. 6.
Soman et al., "Synthesis and Characterization of Stable Fluorocarbon Nanostructures as Drug Delivery Vehicles for Cytolytic Peptides", Nano Lett., 2008, pp. 1131-1136, vol. 8, No. 4.
Soman et al., "Molecularly targeted nanocarriers deliver the cytolytic peptide melittin specifically to tumor cells in mice, reducing tumor growth", The Journal of Clinical Investigation, 2009, pp. 2830-2842, vol. 119, No. 9.
Srivastava et al., "Progress in the Design of Low Molecular Weight Thrombin Inhibitors", Medicinal Research Reviews, 2005, pp. 66-92, vol. 25, No. 1.
Sun et al., "Persistent activation of NF-κb by the Tax transforming protein of HTLV-1: hijacking cellular IκB kinases", Oncogene, 1999, pp. 6948-6958, vol. 18.
Thorek et al., "Superparamagnetic Iron Oxide Nanoparticle Probes for Molecular Imaging", Annals of Biomedical Engineering, 2006, pp. 23-38, vol. 34, No. 1.
Torreri et al., "Biomolecular interactions by Surface Plasmon Resonance technology", Ann 1st Super Sanita, 2005, pp. 437-441, vol. 41, No. 4.
Tran et al., "Association of Hereditary Heparin Co-Factor II Deficiency With Thrombosis", The LANCET, 1985, pp. 413-414, vol. 2.
Turpie, "The top 4 advances in antithrombotic care in the last year", Thrombosis Research, 2008, pp. S2-S6, vol. 123.
Verweij et al., "Paclitaxel (Taxol) and docetaxel (Taxotere): Not simply two of a kind", Annals of Oncology, 1994, pp. 495-505, vol. 5.
Vicente et al., "Antithrombotic activity of dermatan sulfate in heparin cofactor II-deficient mice", Blood, 2004, pp. 3965-3970, vol. 104, No. 13.
Vyavahare et al., "In vitro and in vivo evaluation of the site-specific administration of D-phenylalanyl-L-prolyl-L-arginyl chloromethyl ketone (PPACK): a powerful thrombin inhibitor", Journal of Controlled Release, 1993, pp. 165-173, vol. 27, No. 2.
Wallentin et al., "Ticagrelor versus Clopidogrel in Patients with Acute Coronary Syndromes", The New England Journal of Medicine, 2009, pp. 1045-1057, vol. 361 No. 11.
Weissmann et al., "Effect of melittin upon cellular and lysosomal membranes", Biochemical Pharmacology, 1969, pp. 1771-1775, vol. 18.

(56) References Cited

OTHER PUBLICATIONS

Weitz et al., "Clot-bound Thrombin Is Protected from Inhibition by Heparin-Antithrombin III but Is Susceptible to Inactivation by Antithrombin III-independent Inhibitors", Journal of Clinical Investigation, 1990, pp. 385-391, vol. 86.

Westrick et aL, "Murine Models of Vascular Thrombosis", Arteriosclerosis, Thrombosis, and Vascular Biology, 2007, pp. 2079-2093, vol. 27.

Winter et al., "Molecular Imaging of Angiogenesis in Early-Stage Atherosclerosis With αvβ3-Integrin-Targeted Nanoparticles", Circulation, 2003, pp. 2270-2274, vol. 108.

Winter et al., "Molecular Imaging of Angiogenesis in Nascent Vx-2 Rabbit Tumors Using a Novel αvβ3-targeted Nanoparticle and 1.5 Tesla Magnetic Resonance Imaging", Cancer Research, 2003, pp. 5838-5843, vol. 63.

Winter et al., "Molecular Imaging by MRI", Current Cardiology Reports, 2006, pp. 65-69, vol. 8.

Winter et al., "Emerging nanomedicine opportunities with perfluorocarbon nanoparticles", Expert Rev. Med. Devices, 2007, pp. 137-145, vol. 4, No. 2.

Winter et al., "Antiangiogenic Synergism of Integrin-Targeted Fumagillin Nanoparticles and Atorvastatin in Atherosclerosis", JACC: Cardiovascular Imaging, 2008, pp. 624-634, vol. 1, No. 5.

Xu et al., "Encapsulation of nanosized magnetic iron oxide by polyacrylamide via inverse miniemulsion polymerization", Journal of Magnetism and Magnetic Materials, 2004, pp. 136-143, vol. 277.

Yamaoka et al., "Complementation Cloning of NEMO, a Component of the IκB Kinase Complex Essential for NF-κB Activation", Cell, 1998, pp. 1231-1240, vol. 93.

Yang et al., "Preparation of poly e-caprolactone nanoparticles containing magnetite for magnetic drug carrier", International Journal of Pharmaceutics, 2006, pp. 185-190, vol. 324, No. 2.

Zhou et al. "Suppression of inflammation in a mouse model of rheumatoid arthritis using targeted lipase-labile fumagillin prodrug nanoparticles", Biomaterials, 2012, pp. 8632-8640, vol. 33.

* cited by examiner

LIGAND DIRECTED TOROIDAL NANOPARTICLES FOR THERAPY AND DIAGNOSTIC IMAGING

GOVERNMENT SUPPORT

This invention was made in part with Government support under Grant Number 5 U54 CA119342 awarded by NCI SCCNE. The Government has certain rights in this invention.

FIELD OF THE INVENTION

The present invention generally relates to nanoparticles, methods of making the nanoparticles, and methods of using the nanoparticles to deliver therapeutic agents and/or imaging agents.

BACKGROUND OF THE INVENTION

Noninvasive magnetic resonance (MR) molecular imaging and targeted drug delivery systems, often referred to as theranostic agents, are being developed to enable improved detection, patient risk stratification, site-specific treatment, and longitudinal monitoring. Liposomes may be used as non-toxic, biodegradable drug delivery vehicles. However, the biological instability and rapid uptake of liposomes by the retculoendothelial system (RES) after injection restricts their exploitation in the delivery of therapeutic molecules. As an alternative, polymer vesicles may be used, but the resultant nanoparticles are generally polydisperse and suffer from poor shelf life. Moreover, the preparation of block copolymer requires precipitating the block copolymers using a poor solvent, which is tedious and time consuming. The drug release profiles and in vivo bio-distributive properties of these nanoparticles are not controlled and not well understood. Despite these recent advances in developing contrast and therapeutic agent delivery vehicles, there still is a need for nanoparticle delivery compositions that exhibit greater stability and more controlled drug release.

SUMMARY OF THE INVENTION

Among the various aspects of the invention is the provision of a method for the preparation of a population of self-assembled, substantially bi-concaved disc shaped nanoparticles. Each individual nanoparticle comprises an aqueous inner core and a hydrophilic outer shell comprising an amphiphilic polymer. The process comprises hydrophobically modifying a branched polymer by covalently conjugating amphiphilic lipids to at least 40% of the free reactive groups of the polymer to form an amphiphilic polymer. The process further comprises mixing the amphiphilic polymer with a non polar solvent, and agitating the mixture to form a plurality of inverted micelles comprising the amphiphilic polymer. Lastly, the process further comprises agitating the inverted micelles in the presence of heat and an aqueous solvent to form the self-assembled, bi-concaved disc shaped nanoparticles.

Another aspect of the invention encompasses a substantially bi-concaved disc shaped nanoparticle. The nanoparticle comprises an aqueous inner core and a hydrophilic outer shell comprising an amphiphilic polymer.

A further aspect of the invention provides a method for obtaining an image of a biological tissue of a subject. The method comprises administering a composition comprising a plurality of nanoparticles to the subject. The nanoparticles are substantially bi-concaved disc shaped, and comprise an aqueous inner core and an outer shell comprising an amphiphilic polymer, wherein the surface of the amphiphilic polymer comprises a targeting moiety that selectively targets the nanoparticles to the tissue. The process further comprises performing a signal acquisition scan on the subject, and processing the signal acquisition data to generate an image of the tissue of the subject.

Still another aspect of the invention provides a method for selectively delivering a therapeutic agent to a tissue of a subject. The method comprises administering a composition comprising a plurality of nanoparticles to the subject. The nanoparticles are substantially bi-concaved disc shaped, and comprise an aqueous inner core and an outer shell comprising an amphiphilic polymer. The nanoparticles further comprise a therapeutic agent, and the surface of the outer shell comprises a targeting moiety that selectively targets the nanoparticles to the tissue.

Other aspects and features of the invention are described in more detail below.

DESCRIPTION OF THE FIGURES

The application file contains at least one photograph executed in color. Copies of this patent application publication with color photographs will be provided by the Office upon request and payment of the necessary fee.

DETAILED DESCRIPTION

Figure 1:
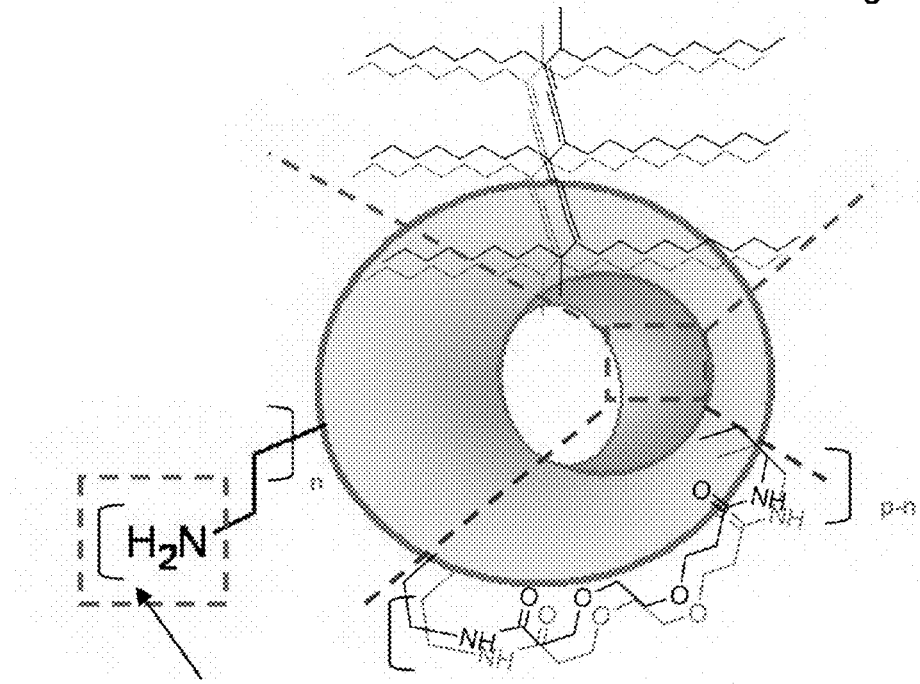
FIG. 1 depicts the general features of a nanoparticle.

The present invention provides substantially bi-concaved disc shaped nanoparticles that may be used to deliver therapeutic agents and/or imaging agents. The substantially bi-concaved disc shaped nanoparticles are self assembled, which means they are relatively quick and easy to prepare. The nanoparticles comprise an amphiphilic branched polymer, and may further comprise targeting moieties, biologically active agents, soluble and insoluble therapeutic agents, and/or imaging agents (e.g., metal atoms, contrast agents, fluorophores) for biological imaging and/or therapeutic targeting. It has been discovered that the bi-concaved disc shape of the nanoparticles provides increased mechanical stability. Furthermore, release of therapeutic compounds from the nanoparticles of the invention is substantially constant and slow.

(I) Nanoparticle

One aspect of the invention provides a substantially bi-concaved disc shaped nanoparticle. The nanoparticle comprises an aqueous inner core and an outer shell comprising an amphiphilic polymer. The nanoparticles of the invention may also comprise biologically active agents, imaging agents, metal atoms, therapeutic agents, targeting moieties, and combinations thereof.

(a) Morphology

The nanoparticle of the invention comprises a substantially bi-concaved disc shape. Within a population of nanoparticles, some of the nanoparticles may comprise a depression, and some of the nanoparticles may comprise a through-hole. In general, at least about 50% of a population of the nanoparticles may be bi-concaved disc shaped. In one embodiment, at least about 75% of a population of nanoparticles may be bi-concaved disc shaped. In another embodiment, at least about 90% of a population of nanoparticles may be bi-concaved disc shaped. In certain embodiments, the percentage of bi-concaved disc shaped nanoparticles may be about 75%, 80%, 85%, 90%, 95%, 97%, or 99% of the total population of nanoparticles.

Because of the shape of the nanoparticle, the diameter of the nanoparticle is greater than the height of the nanoparticle. In general, the diameter of the nanoparticle may range from about 50 nanometers to about 500 nanometers, and the height of the nanoparticle may range from about 20 nanometers to about 150 nanometers. In some embodiments, the diameter of the nanoparticle may range from about 100 nanometers to about 300 nanometers, and the height of the nanoparticle may range from about 40 nanometers to about 85 nanometers. In other embodiments, the diameter of the nanoparticle may range from about 100 nanometers to about 250 nanometers, and the height of the nanoparticle may range from about 30 nanometers to about 80 nanometers. In preferred embodiments, the diameter of the nanoparticle may range from about 120 nanometers to about 250 nanometers, and the height of the nanoparticle may range from about 50 nanometers to about 70 nanometers. In certain preferred embodiments, the diameter of the nanoparticle may be about 100, 110, 120, 130, 140, 150, 160, 170, 180, 190, 200, 210, 220, 230, 240, 250, 260, 270, 280, 290, or 300 nanometers, and the height of the nanoparticle may be about 40, 45, 50, 55, 60, 65, 70, 75, 80, or 85 nanometers.

Typically, the nanoparticles comprising a population of nanoparticles are substantially uniform in size, wherein size is measured as the diameter of a nanoparticle. In general, the variation in size among the nanoparticles of the population is less than about 15%. In preferred embodiments, the variation in size among the nanoparticles of the population may be less than about 10%, and even more preferably less than about 5%. In some embodiments, the variation in size among the nanoparticles of the population may be less than about 10%, 9%, 8%, 7%, 6%, 5%, 4%, 3%, 2%, or 1%.

In general, the bi-concaved disc shaped nanoparticles of the invention have increased stability relative to non-bi-concaved disc shaped nanoparticles. Stability may be measured by changes in the size of the particle over time. In some embodiments, the bi-concaved disc shaped nanoparticles are stable at room temperature for at least several months. In other embodiments, the bi-concaved disc shaped nanoparticles are stable at room temperature for more than two months. In some embodiments, the bi-concaved disc shaped nanoparticles are stable at 4° C. for at least several months. In some embodiments, the bi-concaved disc shaped nanoparticles are stable at 4° C. for more than two months.

(b) Outer Shell

The outer shell of the bi-concaved disc shaped nanoparticle comprises an amphiphilic polymer, wherein the amphiphilic polymer comprises a branched polymer covalently conjugated to amphiphilic lipids. The amphiphilic polymer may comprise from about 1% to about 10% by weight of the nanoparticle. In some embodiments, the amphiphilic polymer may comprise about 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% by weight of the nanoparticle.

(i) Branched Polymers

Non-limiting types of suitable branched polymers include star branched polymers, graft branched polymers, comb branched polymers, brush branched polymers, network branched polymers, hyperbranched polymers, and dendritic polymers.

The polymer may be a synthetic polymer, a semi-synthetic polymer, or a natural polymer. Non-limiting examples of suitable polymers include polyacrylate, polyacrylamide, polyacrylamide sulphonic acid, polyacrylonitrile, polyamines, polyamides, polyamidoamine (PAMAM), polybutadiene, polydimethylsiloxane, polyester, polyether, polyethylene, polyethylene glycol (PEG), polyethyleneimine (PEI), polyethyleneoxide, polyethyleneglycol, polyethyloxazoline, polyhydroxyethylacrylate, polyisoprene, polymethacrylate, polymethacrylamide, polymethylmethacrylate, polymethyloxazoline, polyoxyalkylene oxide, polyphenylene, polypropyleneimine, polypropylene oxide, polystyrene, polyurethane, polyvinyl alcohol, polyvinylpyrrolidone, methylcellulose, carboxymethylcellulose, hydroxyethylcellulose, hydroxypropylcellulose, hydroxypropylmethylcellulose, hyaluronic acid, dextran, dextrin, heparan sulfate, chondroitin sulfate, heparin, alginate, agar, carrageenan, xanthan, guar, polyamino acids (such as e.g., polylysine, polyglycine, and polyserine), co-polymers, and combinations thereof. In a preferred embodiment, the branched polymer may be a polyethyleneimine branched polymer, a PAMAM dendrimer, a star polymer, or graft polymer.

The branched polymer comprises at least one type of reactive group. Suitable reactive groups include, but are not limited to, primary, secondary or tertiary amines, carboxylate, hydroxyl, alkyl, fluoroalkyl, aryl, acetate, amide, ester, sulfone, sulfoxide, sulfonate, sulfonamide, phosphonate, and phosphonamide groups.

The average molecular weight of the branched polymer can and will vary depending on the embodiment. The molecular weight may be expressed as the number average molecule weight ($M_n$) or the weight average molecule weight ($M_w$). In general, the number and weight average molecular weight of the branched polymer may range from about 500 to about 1,000,000 Daltons. In one embodiment, the number and weight average molecular weight of the branched polymer may range from about 500 to about 5,000 Daltons. In another embodiment, the number and weight average molecular weight of the branched polymer may range from about 5,000 to about 50,000. In yet another embodiment, the number and weight average molecular weight of the branched polymer may range from about 50,000 to about 250,000. In a further embodiment, the number and weight average molecular weight of the branched polymer may range from about 250,000 to about 1,000,000. In a preferred embodiment, the number and weight average molecular weight of the branched polymer may be about 10,000 Daltons. In another preferred embodiment, the number and weight average molecular weight of the branched polymer may be about 25,000 Daltons.

(ii) Amphiphilic Lipids

The amphiphilic polymer also comprises amphiphilic lipids covalently conjugated to the branched polymer. In general, at least about 40% of the free reactive groups of the branched polymer are conjugated to amphiphilic lipids. In some embodiments, the percentage of free reactive groups conjugated to amphiphilic lipids may be at least about 40%, 45%, 50%, 55%, 60%, 65%, 70%, or 75%. In other embodiments, the percentage of free reactive groups conjugated to amphiphilic lipids may be greater than 75%. In a preferred embodiment, the percentage of free reactive groups conjugated to amphiphilic lipids may range from about 40% to about 70%. In another preferred embodiment, the percentage of free reactive groups conjugated to amphiphilic lipids may range from about 50% to about 60%. In still another embodiment, the percentage of free reactive groups conjugated to amphiphilic lipids may be about 55%.

Non-limiting examples of suitable amphiphilic lipids include fatty acids, fatty acid esters, phospholipids, bile acids, glycolipids, aliphatic hydrophobic compounds, and aromatic hydrophobic compounds. The amphiphilic lipid may be natural, synthetic, or semi-synthetic. In general, the amphiphilic lipid comprises a polar head group and at least one hydrophobic hydrocarbyl or substituted hydrocarbyl group. The polar head group conjugates the amphiphilic lipid to the branched polymer via a covalent bond. Examples of suitable polar head groups include, but are not limited to, include carboxy, acyl, propargyl, azide, aldehyde, thiol, ester, sulfate, and phosphate. Preferred hydrophobic hydrocarbyl groups include, but are not limited to, alkyl, alkynyl, heterocylic, and combinations thereof. Typically, alkyl or alkynyl groups comprise from about six to about 30 carbon atoms, or more preferably from about 12 to about 24 carbon atoms. In one embodiment, the amphiphilic lipid may be a phospholipid such as, e.g., phosphatidyl ethanolamine, phosphatidyl serine, phosphatidyl inositol, cardiolipin, phosphatidyl ethylene glycol, and the like. In another embodiment, the amphiphilic lipid may be a bile acid such as cholic acid. In a preferred embodiment, the amphiphilic lipid may be a fatty acid, wherein the fatty acid chain comprises an alkyl (saturated) or an alkynyl (unsaturated) group as defined above. Preferred fatty acids include, but are not limited to, 10,12-pentacosadiynoic acid, hexadecyloctadecanoic acid, cholanic acid, linoleic acid, and palmitic acid. In a preferred embodiment, the amphiphilic lipid may be linoleic acid or 10,12-pentacosadiynoic acid.

In an exemplary embodiment, the branched polymer is polyethyleneimine and the amphiphilic lipid is linoleic acid or 10,12-pentacosadiynoic acid, wherein about 55% of the primary amine groups of the polymer are conjugated to the lipid.

(c) Aqueous Inner Core

The nanoparticle of the invention comprises an aqueous inner core. The aqueous inner core may comprise water, a buffer solution, a saline solution, a serum solution, and combinations thereof. The aqueous inner core may also comprise a biologically active agent, an imaging agent, a metal atom, a therapeutic agent, or combinations thereof, as detailed below.

(d) Optional Molecules

The bi-concaved disc shaped nanoparticle of the invention may further comprise at least one molecule selected from the group consisting of a targeting moiety, a biologically active agent, an imaging agent, a metal atom, and a therapeutic agent. The molecule may be water soluble or water insoluble. In one embodiment, the molecule is water soluble and may be contained within the aqueous inner core of the nanoparticle. In another embodiment, the molecule may be conjugated to the surface of the amphiphilic polymer comprising the outer shell of the nanoparticle. In yet another embodiment, the molecule may be conjugated within the hydrophilic region of the amphiphilic polymer comprising the outer shell of the nanoparticle. In still another embodiment, the molecule may be conjugated within the hydrophobic region of the amphiphilic polymer comprising the outer shell of the nanoparticle. It is also envisioned that in nanoparticles comprising more than one optional molecule, the molecules may be localized to different locations of the nanoparticle. In general, the targeting moiety will be conjugated to the surface of the amphiphilic polymer comprising the outer shell of the nanoparticle. As used herein, the term "conjugation" refers to either covalent or non-covalent means. Non-covalent means may include ionic bonding, dative bonding, hydrogen bonding, metallic bonding, and so forth, as well as electrostatic, hydrophobic, and van der Waals interactions.

(i) Metal Atoms

A variety of metal atoms are suitable for inclusion in the nanoparticle of the invention. The metal atom may generally be selected from the group of metal atoms comprised of metals with an atomic number of twenty or greater. For instance, in certain embodiments, the metal atoms may be calcium atoms, scandium atoms, titanium atoms, vanadium atoms, chromium atoms, manganese atoms, iron atoms, cobalt atoms, nickel atoms, copper atoms, zinc atoms, gallium atoms, germanium atoms, arsenic atoms, selenium atoms, bromine atoms, krypton atoms, rubidium atoms, strontium atoms, yttrium atoms, zirconium atoms, niobium atoms, molybdenum atoms, technetium atoms, ruthenium atoms, rhodium atoms, palladium atoms, silver atoms, cadmium atoms, indium atoms, tin atoms, antimony atoms, tellurium atoms, iodine atoms, xenon atoms, cesium atoms, barium atoms, lanthanum atoms, hafnium atoms, tantalum atoms, tungsten atoms, rhenium atoms, osmium atoms, iridium atoms, platinum atoms, gold atoms, mercury atoms, thallium atoms, lead atoms, bismuth atoms, francium atoms, radium atoms, actinium atoms, cerium atoms, praseodymium atoms, neodymium atoms, promethium atoms, samarium atoms, europium atoms, gadolinium atoms, terbium atoms, dysprosium atoms, holmium atoms, erbium atoms, thulium atoms, ytterbium atoms, lutetium atoms, thorium atoms, protactinium atoms, uranium atoms, neptunium atoms, plutonium atoms, americium atoms, curium atoms, berkelium atoms, californium atoms, einsteinium atoms, fermium atoms, mendelevium atoms, nobelium atoms, or lawrencium atoms. In some embodiments, the metal atoms may be selected from the group comprising alkali metals with an atomic number greater than twenty. In other embodiments, the metal atoms may be selected from the group comprising alkaline earth metals with an atomic number greater than twenty. In one embodiment, the metal atoms may be selected from the group of metals comprising the lanthanides. In another embodiment, the metal atoms may be selected from the group of metals comprising the actinides. In still another embodiment, the metal atoms may be selected from the group of metals comprising the transition metals. In yet another embodiment, the metal atoms may be selected from the group of metals comprising the poor metals. In other embodiments, the metal atoms may be selected from the group comprising gold atoms, bismuth atoms, tantalum atoms, and gadolinium atoms. In preferred embodiments, the metal atoms may be selected from the group comprising metals with an atomic number of 53 (i.e. iodine) to 83 (i.e. bismuth). In an alternative embodiment, the metal atoms may be atoms suitable for magnetic resonance imaging. In another alternative embodiment, the metal atoms may be selected from the group consisting of metals that have a K-edge in the x-ray energy band of CT. Preferred metal atoms include, but are not limited to, manganese, iron, gadolinium, gold, and iodine.

The metal atoms comprising the nanoparticle may be metal ions. In some embodiments, the metal atoms may be in the form of +1, +2, or +3 oxidation states. For instance, non-limiting examples include $Ba^{2+}$, $Bi^{3+}$, $Cs^+$, $Ca^{2+}$, $Cr^{2+}$, $Cr^{3+}$, $Cr^{6+}$, $Co^{2+}$, $Co^{3+}$, $Cu^+$, $Cu^{2+}$, $Cu^{3+}$, $Ga^{3+}$, $Gd^{3+}$, $Au^+$, $Au^{3+}$, $Fe^{2+}$, $F^{3+}$, $Pb^{2+}$, $Mn^{2+}$, $Mn^{3+}$, $Mn^{4+}$, $Mn^{7+}$, $Hg^{2+}$, $Ni^{2+}$, $Ni^{3+}$, $Ag^+$, $Sr^{2+}$, $Sn^{2+}$, $Sn^{4+}$, and $Zn^{2+}$. The metal ions may comprise metal complexes, compounds, or chelates. For example, the metal atoms may comprise a complex, chelate, or compound with porphyrin, diethylene triamine pentaacetic acid (DTPA), or tetramethyl heptanedionate (TMHD), 2,4-pentanedione, 1,4,7,10-tetraazacyclododecane-1,4,7,10-tetraacetic acid (DOTA), ethylenediaminetetraacetic acid disodium salt (EDTA), ethyleneglycol-O,O'-bis(2-aminoethyl)-N,N,N',N'-tetraacetic acid (EGTA), N-(2-hydroxyethyl)ethylenediamine-N,N',N'-triacetic acid trisodium salt (HEDTA), nitrilotriacetic acid (NTA), and 1,4,8,11-tetraazacyclotetradecane-N,N',N'',N'''-tetraacetic acid (TETA). These metal complexes, compounds, or chelates may be organo soluble or water soluble. Non-limiting examples of suitable organo soluble complexes include pentanedione-gadolinium (III), bismuthneodecanoate, iohexol and related compounds, and organo soluble complexes of gold. Exemplary water soluble metal chelates or complexes include, but are not limited to, Mn-DTPA, Mn-porphyrin, and Gd-DTPA.

In some embodiments, the metal atoms may comprise a metal oxide. For instance, non-limiting examples of metal oxides may include iron oxide, manganese oxide, or gadolinium oxide. Additional examples may include magnetite, maghemite, or a combination thereof. In certain embodiments, the metal oxide may have the formula $MFe_2O_4$, where M is selected from the group comprising Fe, Mn, Co, Ni, Mg, Cu, Zn, Ba, Sr or a combination thereof. In various embodiments, the metal oxide is magnetic. In a preferred embodiment, the metal atom may comprise iron oxide. In several embodiments, the nanoparticle may comprise both a metal oxide and an additional metal as described herein. For instance, the nanoparticle may comprise a metal oxide and an additional metal such as iodine, gadolinium, bismuth, or gold. Generally speaking, a metal oxide included in a nanoparticle of the invention is between about 1 and about 30 nm in diameter. For example, the metal oxide may be about 1, 2, 3, 4, 5, 10, 15, 20, 25, or 30 nm in diameter.

Typically, the nanoparticle comprises at least 50,000 metal atoms. In some embodiments, the nanoparticle may comprise at least 100,000, at least 150,000, at least 200,000, at least 250,000, at least 300,000, at least 350,000, or at least 400,000 metal atoms.

(ii) Biologically Active Agent

The bi-concaved disc shaped nanoparticle of the invention may also comprise at least one biologically active agent. Non-limiting examples of suitable biologically active agents include pharmaceuticals, therapeutic agents, diagnostic agents, radioactive isotopes, genetic materials, proteins, carbohydrates, lipids, nucleic acid based materials, and combinations thereof. The biologically active may be in its native form or it may be derivatized with hydrophobic or charged moieties to enhance incorporation or adsorption to the nanoparticle. Accordingly, the biologically active may be water soluble or water insoluble. As detailed above, the biologically active may be contained within the aqueous inner core, conjugated to the surface of the amphiphilic polymer comprising the outer shell, conjugated within the hydrophilic region of the amphiphilic polymer comprising the outer shell, or conjugated within the hydrophobic region of the amphiphilic polymer comprising the outer shell.

Non-limiting examples of biologically active agents may include immune-related agents, thyroid agents, respiratory products, antineoplastic agents, anti-helmintics, anti-malarials, mitotic inhibitors, hormones, anti-protozoans, anti-tuberculars, cardiovascular products, blood products, biological response modifiers, anti-fungal agents, vitamins, peptides, anti-allergic agents, anti-coagulation agents, circulatory drugs, metabolic potentiators, anti-virals, anti-anginals, antibiotics, anti-inflammatories, anti-rheumatics, narcotics, cardiac glycosides, neuromuscular blockers, sedatives, local anesthetics, general anesthetics, or radioactive atoms or ions. Non-limiting examples of biologically active agents are included in Table A below. Additionally, a nanoparticle of the invention may comprise two or more, three or more, or four or more biologically active agents.

TABLE A

Non-limiting Examples of Biologically Active Agents.

| Agent | Non-limiting examples |
|---|---|
| Immune-related agents | immune serums, antitoxins, antivenoms bacterial vaccines, viral vaccines, rabies prophylaxis products |
| thyroid agents | iodine products and anti-thyroid agents |
| respiratory products | xanthine derivatives theophylline and aminophylline |
| antineoplastic agents | platinum compounds (e.g., spiroplatin, cisplatin, and carboplatin), methotrexate, fluorouracil, adriamycin, mitomycin, ansamitocin, bleomycin, cytosine arabinoside, arabinosyl adenine, mercaptopolylysine, vincristine, busulfan, chlorambucil, melphalan (e.g., PAM, L-PAM or phenylalanine mustard), mercaptopurine, mitotane, procarbazine hydrochloride dactinomycin (actinomycin D), daunorubicin hydrochloride, doxorubicin hydrochloride, paclitaxel and other taxenes, rapamycin, manumycin A, TNP-470, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase) Erwina asparaginase, interferon α-2a, interferon α-2b, teniposide (VM-26), vinblastine sulfate (VLB), vincristine sulfate, bleomycin sulfate, hydroxyurea, procarbazine, dacarbazine, camptothecin |
| anti-helmintics | pyrantel pamoate, piperazine, tetrachloroethylene, thiabendazole, niclosamide |
| antimalarials | chloroquine, amodiaquine, antifolate drugs, proguanil (chloroguanide), mefloquine, quinine, halofantrine, artemesinin and derivatives, primaquine, doxycycline, tetracycline, and clindamycin |
| mitotic inhibitors | etoposide, colchicine, and the vinca alkaloids |
| hormones | androgens, progestins, estrogens and antiestrogens, growth hormone, melanocyte stimulating hormone, estradiol, beclomethasone dipropionate, betamethasone, betamethasone acetate and betamethasone sodium phosphate, vetamethasone disodium phosphate, vetamethasone sodium phosphate, cortisone acetate, dexamethasone, dexamethasone acetate, dexamethasone sodium phosphate, flunisolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisolone acetate, prednisolone sodium phosphate, prednisolone tebutate, prednisone, triamcinolone, triamcinolone acetonide, triamcinolone diacetate, triamcinolone hexacetonide, fludrocortisone acetate, oxytocin, vassopressin, glucagon and their derivatives |
| antiprotozoans | chloroquine, hydroxychloroquine, metronidazole, quinine and meglumine antimonite |
| antituberculars | para-aminosalicylic acid, isoniazid, capreomycin sulfate cycloserine, ethambutol hydrochloride ethionamide, pyrazinamide, rifampin, and streptomycin sulfate |
| cardiovascular products | chelating agents and mercurial diuretics and cardiac glycosides |
| blood products | parenteral iron, hemin, hematoporphyrins and their derivatives |
| biological response modifiers | muramyldipeptide, muramyltripeptide, microbial cell wall components, lymphokines (e.g., bacterial endotoxin such as lipopolysaccharide, macrophage activation factor), sub-units of bacteria (such as Mycobacteria, Corynebacteria), the synthetic dipeptide N-acetyl-muramyl-L-alanyl-D-isoglutamine |
| anti-fungal agents | ketoconazole, nystatin, griseofulvin, flucytosine (5-fc), fumagillin, miconazole, amphotericin B, ricin, cyclosporins, and β-lactam antibiotics (e.g., sulfazecin) |
| vitamins | cyanocobalamin neinoic acid, retinoids and derivatives such as retinol palmitate, and α-tocopherol |
| peptides | manganese super oxide dismutase; enzymes such as alkaline phosphatase |
| anti-allergic agents | amelexanox |
| anti-coagulation agents | phenprocoumon and heparin |
| circulatory drugs | propranolol |
| metabolic potentiators | glutathione |
| antivirals | acyclovir, amantadine azidothymidine (AZT, DDI, Foscarnet, or Zidovudine), ribavirin and vidarabine monohydrate (adenine arabinoside, ara-A) |
| antianginals | diltiazem, nifedipine, verapamil, erythritol tetranitrate, isosorbide dinitrate, nitroglycerin (glyceryl trinitrate) and pentaerythritol tetranitrate |
| antibiotics | dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin including penicillin G and penicillin V, ticarcillin rifampin, aminoglycosides and tetracycline |
| antiinflammatories | diflunisal, ibuprofen, indomethacin, meclofenamate, mefenamic acid, naproxen, oxyphenbutazone, phenylbutazone, piroxicam, sulindac, tolmetin, aspirin and salicylates |
| antirheumatics | adalimumab, azathioprine, chloroquine and hydroxychloroquine (antimalarials), cyclosporine (Cyclosporin A), D-penicillamine, etanercept, gold salts (sodium aurothiomalate, auranofin), infliximab, leflunomide, methotrexate, minocycline (a tetracycline antibiotic), sulfasalazine |
| narcotics | paregoric, opiates, codeine, heroin, methadone, morphine and opium |
| cardiac glycosides | deslanoside, digitoxin, digoxin, digitalin and digitalis |

TABLE A-continued

Non-limiting Examples of Biologically Active Agents.

| Agent | Non-limiting examples |
|---|---|
| neuromuscular blockers | atracurium mesylate, gallamine triethiodide, hexafluorenium bromide, metocurine iodide, pancuronium bromide, succinylcholine chloride (suxamethonium chloride), tubocurarine chloride and vecuronium bromide |
| sedatives (hypnotics) | amobarbital, amobarbital sodium, aprobarbital, butabarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, pentobarbital sodium, phenobarbital sodium, secobarbital sodium, talbutal, temazepam and triazolam |
| local anesthetics | bupivacaine hydrochloride, chloroprocaine hydrochloride, etidocaine hydrochloride, lidocaine hydrochloride, mepivacaine hydrochloride, procaine hydrochloride and tetracaine hydrochloride |
| general anesthetics | droperidol, etomidate, fentanyl citrate with droperidol, ketamine hydrochloride, methohexital sodium and thiopental sodium |
| radioactive particles or ions | strontium, iodide rhenium, yttrium, and radiopharmaceuticals, such as radioactive iodine and phosphorus product |

In some embodiments, the biologically active agent may also be a targeting moiety (see below). For instance, an antibody, nucleic acid, peptide fragment, small organic molecule, or a mimetic of a biologically active ligand may be a therapeutic agent, such as an antagonist or agonist, when bound to specific epitopes. As an example, antibody against αvβ3 integrin on neovascular endothelial cells has been shown to transiently inhibit growth and metastasis of solid tumors. Thus, in another embodiment of the invention, the targeting moiety and the therapeutic agent may be constituted by a single component which functions both to target the nanoparticle and to provide the therapeutic agent to the desired site.

The amount of therapeutic agent incorporated into a nanoparticle will vary. Those of skill in the art will appreciate that the loading rate will depend upon the type of therapeutic agent and the intended target, for example. In general, at least about 5% by weight of the amphiphilic polymer may comprise a therapeutic agent. In some embodiments, the therapeutic agent may comprise at least about 4.5%, 4%, 3.5%, 3%, 2.5%, 2%, 1.5%, 1%, or 0.5% by weight of the amphiphilic polymer.

Figure 17:
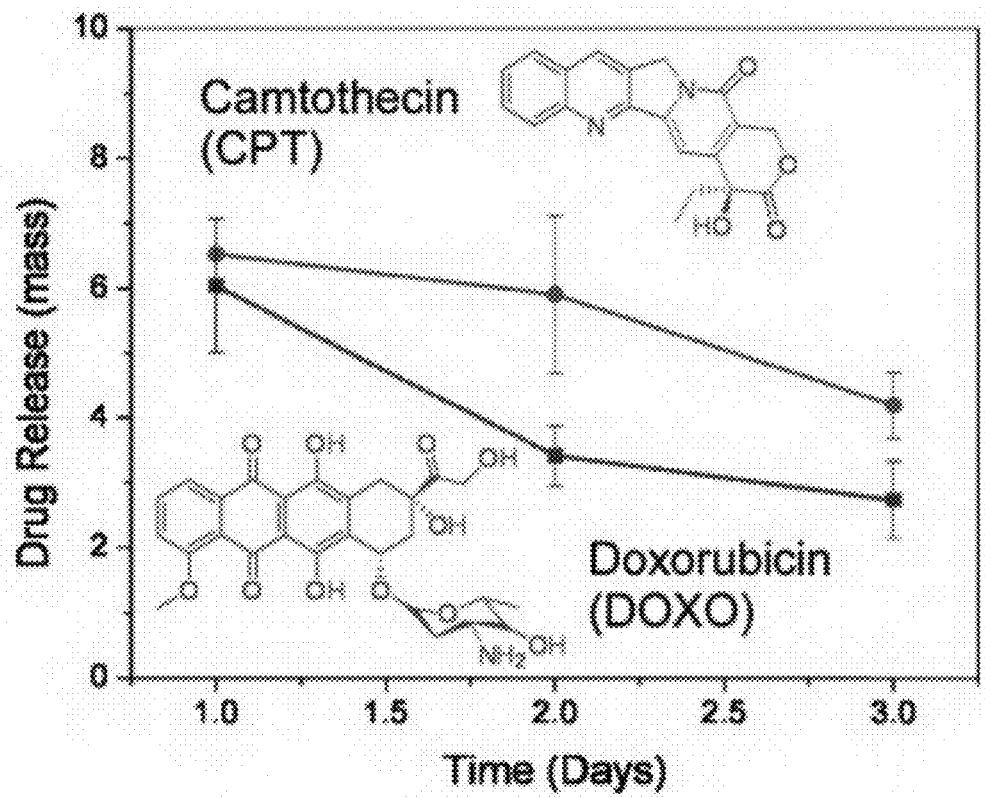
FIG. 17 depicts dissolution assays: cumulative percent drug release in vitro from nanoparticles in dissolution over 3 days at 37° C.

The rate of release of the therapeutic agent can and will vary depending upon the nature of the therapeutic agent, the location of the therapeutic agent in the nanoparticle, and the composition of the amphiphilic polymer comprising the outer shell of the nanoparticle. In general, the rate of release is substantially constant (e.g., see FIG. 17). In one embodiment, the therapeutic agent may be released over a period of time ranging from about 1 day to about 1 month. In other embodiments, the therapeutic agent may be released over a period of time of about one week, 2 weeks, or three weeks. In a further embodiment, the therapeutic agent may be released over a period of time that is greater than one month. The rate of release may be decreased by cross-linking the amphiphilic polymer of the nanoparticle as detailed below.

(iii) Targeting Moiety

In some embodiments, the bi-concaved disc shaped nanoparticle of the invention may also comprise a targeting moiety. A targeting moiety directs or targets the nanoparticle to a particular site or location. Targeted particles may include a wide variety of targeting moieties conjugated to the surface of the outer shell, including but not limited to, antibodies, antibody fragments, peptides, small molecules, polysaccharides, nucleic acids, aptamers, peptidomimetics, other mimetics and drugs alone or in combination. These targeting moieties may be utilized to specifically bind the nanoparticles to cellular epitopes and/or receptors. The targeting moieties may be conjugated directly or indirectly to the nanoparticle.

Direct conjugation of the targeting moieties to the nanoparticle refers to the preparation of a targeting moiety-nanoparticle complex wherein the targeting moiety is either adsorbed through ionic, electrostatic, hydrophobic or other non-covalent means to the nanoparticle surface (e.g., via an acylated-antibody or hybridization between complementary nucleic acid sequences), or chemically linked to the surface of the outer shell through covalent bonds to a component of the conjugated lipids, or intrinsically incorporated into the amphiphilic polymer of the outer shell (e.g., a lipid derivatized to a peptidomimetic agent). The targeting moiety also may be directly conjugated to the nanoparticle via a linker molecule. A linker molecule comprises at least two functional groups such that the linker molecule is disposed between the nanoparticle and the targeting moiety.

Indirect conjugation refers to forming the complex between the nanoparticle and the targeting moiety in vivo in two or more steps. Indirect conjugation utilizes a chemical linking system to produce the close and specific apposition of the nanoparticle to a targeted cell or tissue surface. A non-limiting example of an indirect targeting system is avidin-biotin.

Avidin-biotin interactions are useful non-covalent targeting systems that have been incorporated into many biological and analytical systems and selected in vivo applications. Avidin has a high affinity for biotin ($10^{-15}$ M) facilitating rapid and stable binding under physiological conditions. Targeted systems utilizing this approach are administered in two or three steps, depending on the formulation. Typically, a biotinylated ligand, such as a monoclonal antibody, is administered first and "pretargeted" to the unique molecular epitopes. Next, avidin is administered, which binds to the biotin moiety of the "pretargeted" ligand. Finally, the biotinylated nanoparticle is added and binds to the unoccupied biotin-binding sites remaining on the avidin, thereby completing the biotinylated ligand-avidin-particle "sandwich." The avidin-biotin approach may avoid accelerated, premature clearance of targeted nanoparticles by the mononuclear phagocyte system (MPS) secondary to the presence of surface antibody. Additionally, avidin, with four independent biotin-binding sites provides signal amplification and improves detection sensitivity.

Targeting moieties may be chemically attached to the surface of nanoparticles by a variety of methods depending upon the nature of the targeting moiety and composition of the nanoparticle surface. Direct chemical conjugation of targeting moieties to proteinaceous nanoparticles often take advantage of numerous amino-groups (e.g. lysine) inherently present within the surface. Alternatively, functionally active chemical groups such as pyridyldithiopropionate, maleimide or aldehyde may be incorporated into the surface as chemical "hooks" for targeting molecule conjugation after the nanoparticles are formed. Another common post-processing approach is to activate surface carboxylates with carbodiimide prior to targeting molecule addition.

In yet another embodiment, the targeting moiety may be covalently attached via "click chemistry". Recent years have also witnessed rapid advancement in the synthetic methodologies based on "click" reactions. "Click-chemistry" techniques are gaining wide acceptance mainly due to high reliability, tolerance to a broad variety of functional groups, quantitative yields, and their applicability under mild reaction conditions. The ability to reduce Cu catalyst in situ has now allowed "click-chemistry" to be performed in aqueous environment and thereby resolves the oxidative instability of the catalyst under aerobic conditions.

The selected covalent linking strategy is primarily determined by the chemical nature of the targeting moiety. For instance, monoclonal antibodies and other large proteins may denature under harsh processing conditions whereas the bioactivity of carbohydrates, short peptides, aptamers, drugs or peptidomimetics often can be preserved under these conditions.

To ensure high targeting moiety binding integrity and maximize targeted nanoparticle avidity, flexible spacer arms, e.g. polyethylene glycol, amino acids, long or short chain hydrocarbons, sugars (e.g. polydextrose), nucleic acids, aptamers, or simple caproate bridges, may be inserted between an activated surface functional group and the targeting moiety. These extensions may be 2 nm or longer and may minimize interference of targeting moiety binding by nanoparticle surface interactions.

(iv) Imaging Agents

In further embodiments, the bi-concaved disc shaped nanoparticle of the invention may also comprise an imaging agent. In one embodiment, the imaging agent may comprise a metal atom, as detailed above. In another embodiment, the imaging agent may be a radionuclide. Non-limiting examples of suitable radionuclides include technetium-99m, ilodine-123 and 131, thallium-201, gallium-67, fluorine-18, fluorodeoxyglucose, and indium-111. In yet another embodiment, the imaging agent may be a fluorophore. Suitable fluorophores include, but are not limited to, fluorescein isothiocyante (FITC), fluorescein thiosemicarbazide, rhodamime, Texas Red, CyDyes (e.g., Cy3, Cy5, Cy5.5), Alexa Fluors (e.g., Alexa$^{488}$, Alexa$^{555}$, Alexa$^{594}$; Alexa$^{647}$), and near infrared (NIR) (700-900 nm) fluorescent dyes.

(e) Optional Cross-Linking

The amphiphilic polymer of the outer shell of the nanoparticle may be optionally cross-linked. The degree of cross-linking may control the release of therapeutic agents from the outer shell or the aqueous inner core of the nanoparticle. Cross-linking may also impart increased mechanical stability to the nanoparticle. The surface lipids of the amphiphilic polymer of the outer shell may be cross-linked by chemical means. Alternatively, the core polymer of the amphiphilic polymer may be cross-linked by photo-chemical means. Generally, at least about 50% of the available reactive groups of the amphiphilic polymer may be cross-linked. In some embodiments, more than 50%, 60%, 70%, 80%, 90%, or 95% of the available reactive groups of the amphiphilic polymer may be cross-linked. Suitable means of cross-linking are detailed below in section (II).

(f) Optional Pegylation

In still other embodiments, the amphiphilic polymer of the nanoparticle may be derivatized with polyethylene glycol (PEG), as detailed below in section (II).

(II) Methods of Making Nanoparticles

Another aspect of the present invention is a process for the preparation of a population of self-assembled, substantially bi-concaved disk shaped nanoparticles of the invention. Generally speaking, the process comprises, in part, forming an amphiphilic polymer, forming a plurality of inverted micelles comprising the amphiphilic polymer, and self-assembly of the substantially bi-concaved disk shaped nanoparticles of the invention. In some embodiments, the nanoparticle may comprise at least one molecule selected from the group consisting of a biologically active agent, a metal atom, a therapeutic agent, and a targeting moiety. In other embodiments, the nanoparticle may be pegylated. In further embodiments, the nanoparticle may be cross-linked.

(a) Forming an Amphiphilic Polymer

The process for the preparation of a particle of the invention comprises, in part, forming an amphiphilic polymer. Generally speaking, the process comprises hydrophobically modifying a branched polymer by covalently conjugating an amphiphilic lipid to the branched polymer. Suitable branched polymers and amphiphilic lipids are detailed in section (I) above. As described above, the branched polymers comprise free reactive groups. In an exemplary embodiment, the free reactive groups are amine groups.

Generally speaking, at least 40% of the free reactive groups of the polymer are conjugated with amphiphilic lipid. In some embodiments, about 50% to about 65% of the free reactive groups of the polymer are conjugated with lipid. In other embodiments, about 55% to about 60% of the free reactive groups of the polymer are conjugated with lipid. In certain embodiments, about 40, 45, 50, 51, 52, 53, 54, 55, 56, 57, 58, 59, 60, 61, 62, 63, 64, or 65% of the free reactive groups of the polymer are conjugated with lipid.

The molar ratio of polymer to amphiphilic lipid is typically from about 1:0.4 to about 1:0.8. In some embodiments, molar ratio of polymer to amphiphilic lipid may be about 1:0.4, 1:0.45, 1:0.5, 1:0.55, 1:0.6, 1:0.65, 1:0.7, 1:0.75, or 1:0.8.

Methods of covalently conjugating an amphiphilic lipid to a polymer are known in the art and detailed in the examples. Briefly, an active group of the polymer forms a covalent bond with an active group of the amphiphilic lipid. Suitable polymer active groups are detailed above. An amphiphilic lipid may comprise a suitable active group for forming a bond with the polymer active group (i.e. direct conjugation), or may be treated with a linker to provide a suitable active group (i.e. indirect conjugation). Non-limiting examples of active groups may include epoxides, carboxylates, oxiranes, esters of N-hydroxysuccinimide, aldehydes, hydrazines, maleimides, mercaptans, amino groups, alkylhalides, isothiocyanates, carbodiimides, diazo compounds, tresyl chloride, tosyl chloride, propargyl, azide, and trichloro S-triazine. In some embodiments, the reactive groups may be photoreactive groups, that when contacted with light may become activated, and capable of covalently attaching to the polymer reactive groups. Exemplary photo-reactive groups may include aryl azides, diazarenes, beta-carbonyldiazo, and benzophenones. The reactive species are nitrenes, carbenes, and radicals. These reactive species are generally capable of covalent bond formation. In a preferred embodiment, the reactive groups are carboxyl and amine.

(b) Forming a Plurality of Inverted Micelles

The process for the preparation of a particle of the invention further comprises, in part, forming a plurality of inverted micelles. Generally speaking, the unimolecular inverted micelles (i.e., reversed micelles) are formed by agitating a mixture of the amphiphilic polymer from step (a) above with a non-polar solvent. Typically, the concentration of amphiphilic polymer in the non-polar solvent is about $10^{-7}$ to about $10^{-5}$ M. In some embodiments, the concentration of amphiphilic polymer is about $10^{-6}$ M.

In some embodiments, the non-polar solvent is organic. Non-limiting examples of non-polar solvents may include acetone, methyl acetate, ethyl acetate, hexane, benzene, toluene, diethyl ether, dichloromethane, and chloroform. In an exemplary embodiment, the solvent is chloroform or dichloromethane.

The mixture may be agitated through physical inversion, vortexing, mixing, shaking, sonicating, stirring, or other similar means. Typically, the mixture may be agitated for about 1 min to about 10 min, although longer agitation times may be possible. In some embodiments, the mixture may be agitated for about 1, 2, 3, 4, 5, 6, 7, 8, 9, or 10 min. Generally speaking, the agitation is performed at about 4° C. to about room temperature.

(c) Self-Assembly of a Bi-Concaved Disc Shaped Nanoparticle

After formation of the plurality of inverted micelles in step (b) above, the process of the invention comprises the self-assembly of the inverted micelles into a bi-concaved disc shaped nanoparticle of the invention. Generally speaking, the process comprises agitating the inverted micelles in the presence of heat and a solvent system.

The temperature during the agitating dictates, in part, the size of the resulting nanoparticles. Typically, as the temperature increases, the size of the nanoparticles increase. In one embodiment, the temperature during the agitation may range from about 30° C. to about 65° C. For instance, the temperature may be about 30, 35, 40, 45, 50, 55, 60, or 65° C.

The mixture may be agitated via physical or acoustical means. For instance, the mixture may be agitated by physical inversion, vortexing, mixing, shaking, sonicating, or other similar means. Preferably, the mixture may be agitated by high shear mixing. Generally, the inverted micelles are agitated for about 15 min to about 90 min. In some embodiments, the inverted micelles are agitated for about 30 min to about 60 min. In other embodiments, the inverted micelles are agitated for about 20, 25, 20, 35, 40, 45, 50, 55, 60, 65 or 70 min.

The inverted micelles are typically agitated, with heat, in the presence of a solvent system. In some embodiments, the solvent system comprises both a polar solvent and a non-polar solvent. For instance, in certain embodiments, the polar solvent is an aqueous solvent and the non-polar solvent is an organic solvent. By way of example, the non-polar solvent may be the non-polar solvent used in step (b) above, and the aqueous solvent may be added, with brief agitation, to the non-polar solvent. To achieve an appropriate ratio between the polar and non-polar solvent, the non-polar solvent may be evaporated from the mixture. In a certain embodiment the weight ratio of the polar and non polar solvent may be about 1:5. For more details, see the examples. In an exemplary embodiment, the polar solvent is water and the non-polar solvent is chloroform.

To achieve an appropriate ratio between the polar and non-polar solvent, the non-polar solvent may be evaporated from the mixture. In some embodiments, the evaporation may be performed under reduced pressure. Generally speaking, the pressure selected will depend, in part, on the non-polar solvent. In some embodiments, the reduced pressure may be between about 350 mbar and 1000 mbar. In other embodiments, the reduced pressure may be about 400, 450, 500, 550, 600, 650, 700, 750, 800, 850, 900, or 950 mbar. When the non-polar solvent is chloroform, the reduced pressure may be between about 400 and about 500 mbar. For instance, the reduced pressure may be between about 400 mbar and about 450 mbar, or between about 420 mbar and about 440 mbar.

(d) Optional Molecules

In certain embodiments, a nanoparticle of the invention may further comprise at least one molecule selected from the group consisting of a targeting moiety, a biologically active agent, a contrast agent, a metal atom, and a therapeutic agent. Suitable molecules are detailed above. These molecules may be conjugated to the surface of the outer shell of the nanoparticle, conjugated within the hydrophilic region of the amphiphilic polymer comprising the outer shell, conjugated within the hydrophobic region of the amphiphilic polymer comprising the outer shell, or contained within the inner core of the nanoparticle.

In one embodiment, the molecule may be incorporated into the outer shell of the nanoparticle. To incorporate such a molecule, the targeting moiety, biologically active agent, imaging agent, metal atom, or therapeutic agent is typically added to the mixture comprising a plurality of inverted micelles in a non polar solvent described in step (b) above. After mixing, the molecule is incorporated into the micelles by phase transition from aqueous to organic phase. As a result, after self-assembly, the molecule is incorporated into the outer shell of the nanoparticle.

In another embodiment, a water soluble biologically active agent, imaging agent, metal atom, or therapeutic agent may be incorporated into the inner core of the nanoparticle. To incorporate such a molecule, the biologically active agent, imaging agent, metal atom, or therapeutic may be transferred to the interior of the inverted micelle. For instance, after formation of the plurality of micelles, but before the self-assembly of the nanoparticles of the invention, the plurality of micelles may be mixed with the water soluble molecule. The mixture may be agitated, and as a result, the water soluble molecule is transferred to the interior of the inverted micelles, and consequently, to the inner core of the nanoparticle after the self-assembly of the inverted micelles. Typically, only minimal agitation is required, and in most embodiments, physical inversion is sufficient to transfer the water soluble molecules to the interior of the inverse micelles.

In another embodiment, a water insoluble targeting moiety, metal atom, biologically active agent, imaging agent, or therapeutic agent may be located within the hydrophobic region of the amphiphilic polymer comprising the outer shell of the nanoparticle. To incorporate such a molecule, the water insoluble molecule may be dissolved in organic non polar solvent and mixed with the inverted micelles. Consequently, the water insoluble molecule is transferred to the hydrophobic region of the amphiphilic polymer after the self-assembly of the inverted micelles.

In yet another embodiment, a targeting moiety, biologically active agent, imaging agent, metal atom, or therapeutic agent may be located within the hydrophilic region of the amphiphilic polymer or the surface of the outer shell of the nanoparticle. In these embodiments, the molecule may be adsorbed to the surface through non-covalent bonds, or covalently bonded to the amphiphilic polymer. For instance, the molecule may be bonded to the surface of the nanoparticle through covalent bonding, dative bonding, ionic bonding, hydrogen bonding or Van der Waals bonding.

(e) Cross-Linking

After the self-assembly of a nanoparticle of the invention, the outer shell may be cross-linked. As detailed above, cross-linking may be used to alter the rate of release of a therapeutic molecule. Alternatively, cross-linking may be used to increase the stability of the nanoparticle. In some embodiments, the particles may be cross-linked on the surface of the outer shell. In other embodiments, the particles may be cross-linked within the outer shell. The cross-linking may be chemical cross-linking or photochemical cross-linking. Methods of cross-linking are known in the art. Briefly, suitable cross-linkers will react with one or more active groups of the amphiphilic polymer. Cross-linkers may be homobifunctional or heterobifunctional. Suitable chemical cross-linkers may include glutaraldehyde, bis-carboxylic acid spacers, or bis-carboxylic acid-active esters. In a preferred embodiment, photochemical cross-linking may be achieved by uv-crosslinking of polydiacetylinic bonds. One of ordinary skill in the art would recognize that a suitable cross-linker can and will vary depending on the composition of the nanoparticle and the intended use.

(f) Pegylation

In certain embodiments, a particle of the invention may be pegylated. As used herein, "pegylation" refers to the addition of polyethylene glycol to the outer shell. Methods of pegylation are commonly known in the art and detailed in the examples. In some embodiments, the pegylation may be used to decrease the zeta surface charge of the nanoparticle. Stated another way, pegylation may be used to impart a negative charge to the surface of the nanoparticle. In some embodiments, the pegylation may be used to alter the in vivo circulation of the nanoparticle.

(III) Methods of Using Nanoparticles

A further aspect of the invention encompasses methods of using the bi-concaved shaped nanoparticles to deliver imaging agents and/or therapeutic agents to a subject. Typically, the nanoparticles of the invention are formulated as a composition for in vivo, in vitro, in situ, or ex vivo use. The size of nanoparticles utilized in a composition will vary depending upon the composition of the nanoparticle, the method of making the nanoparticle, and the intended use of the nanoparticle. Average sizes of nanoparticles in a population is detailed above in section (I)(a).

The composition comprising a plurality of nanoparticles may be a solution, a mixture, or a suspension. In one embodiment, the composition may be a solution. In another embodiment, the composition may be a mixture. In another embodiment, the composition may be a suspension. A non-limiting example of a suspension is a colloid. In some embodiments, the composition may be a colloid. Generally speaking a colloid is a suspension of fine particles that do not readily settle out of the suspension.

The composition of nanoparticles of the invention may be administered to a subject to enable a therapeutic treatment and/or imaging of a biological tissue. Suitable subjects include, but are not limited to, mammals, amphibians, reptiles, birds, fish, and insects. In a preferred embodiment, the subject is a human.

The composition may be formulated and administered to a subject by several different means that will deliver an effective dose for imaging. Such compositions may generally be administered parenterally, intraperitoneally, intravascularly, or intraplumonarily in dosage unit formulations containing conventional nontoxic pharmaceutically acceptable carriers, adjuvants, excipients, and vehicles as desired. The term parenteral as used herein includes topical, subcutaneous, intravenous, intramuscular, intraperitoneal, intracystic, intrauterine, intraauricular, intranasal, ocular, intraocular, intrapulmonary, oral, intrapharyngeal, transrectal, intra or transurethral, intrauterine, intravaginal, or intrasternal injection, infusion, spraying (fine or coarse), direct and indirect topical application, or aerosol techniques.

In one embodiment, the composition may be administered in a bolus. In a preferred embodiment, the composition may be administered intravenously. Formulation of pharmaceutical compositions is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above are also useful.

For imaging purposes, formulations for parenteral administration may be in the form of aqueous or non-aqueous isotonic or hypotonic sterile injection solutions or suspensions. These solutions and suspensions may be prepared from sterile powders or granules having one or more carriers or diluents. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

One of skill in the art will recognize that the amount and concentration of the composition administered to a subject for therapeutic treatment and/or imaging will depend in part on the subject and the tissue to be imaged.

In some embodiments, the composition comprising the nanoparticles of the invention may be used to image biological tissue. The imaging may be performed in vitro, ex vivo, in situ, or in vivo. Suitable imaging techniques to be used in conjunction with compositions comprising the nanoparticles of the invention may include CT imaging, spectral CT imaging, nuclear imaging (e.g., PET), near infra red (NIR) imaging, optical imaging, magnetic resonance (MR) imaging, photoacoustic imaging, and combinations thereof. Advantageously, nanoparticles of the invention may be used in multi-modality imaging. In addition, nanoparticles of the invention may be used for both steady-state acquisition and first pass acquisition. A nanoparticle of the invention may be simultaneously used for imaging and therapeutic agent delivery, imaging alone, or therapeutic agent delivery alone.

Biological tissue, as used herein, may refer to cells, organs, tumors, or material associated with cells, organs, or tumors, such as blood clots. Suitable tissues may include, but are not limited to, heart, lungs, brain, eye, stomach, spleen, bones, pancreas, gall bladder, kidneys, liver, intestines, skin, uterus, bladder, eyes, lymph nodes, blood vessels, and blood and lymph components. A non-limiting example of a blood component is a microthrombus. In some embodiments, a nanoparticle of the invention may be used to image angiogenesis. In other embodiments, a nanoparticle of the invention may be used for volume imaging in a biological tissue. Suitable tissues include, but are not limited to blood vessels, lymphatic vessels, or extravascular tissues. The imaged tissue may be associated with at least one pathology selected from the group consisting of oncologic, cardiovascular, dermatological, urogenital, pulmonary, muscular skeletal, gastrointestinal, neurological, hematologic, endocrine, sensory organ, inflammatory and rheumatologic diseases.

Depending upon the type of imaging, the metal comprising the nanoparticle will be appropriate for the selected imaging type. For instance, for CT imaging, the metal will be selected from the group of metals consisting of metals that have a K-edge within the x-ray energy band of CT. Additionally, the amount of metal that comprises the nanoparticle can and will vary depending on the intended method of imaging. For example, for CT imaging, the nanoparticle will generally comprise from about 100,000 to about 500,000 metal atoms. For PET nuclear imaging, the nanoparticle will generally comprise from about 1 to about 6 metal atoms. For MR imaging, the nanoparticle will generally comprise at least about 100,000 metal atoms.

DEFINITIONS

The term "acyl," as used herein alone or as part of another group, denotes the moiety formed by removal of the hydroxy group from the group COOH of an organic carboxylic acid, e.g., RC(O), wherein R is R1, R1O—, R1R2N—, or R1S—, R1 is hydrocarbyl, heterosubstituted hydrocarbyl, or heterocyclo, and R2 is hydrogen, hydrocarbyl or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The term "aryl" or "Ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The term "heteroaryl" as used herein alone or as part of another group denote optionally substituted aromatic groups having at least one heteroatom in at least one ring, and preferably 5 or 6 atoms in each ring. The heteroaryl group preferably has 1 or 2 oxygen atoms and/or 1 to 4 nitrogen atoms in the ring, and is bonded to the remainder of the molecule through a carbon.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples are included to demonstrate preferred embodiments of the invention. It should be appreciated by those of skill in the art that the techniques disclosed in the following examples represent techniques discovered by the inventors to function well in the practice of the invention. Those of skill in the art should, however, in light of the present disclosure, appreciate that many changes could be made in the specific embodiments that are disclosed and still obtain a like or similar result without departing from the spirit and scope of the invention, therefore all matter set forth is to be interpreted as illustrative and not in a limiting sense.

Example 1

Preparation of Nanoparticles

Figure 2A:
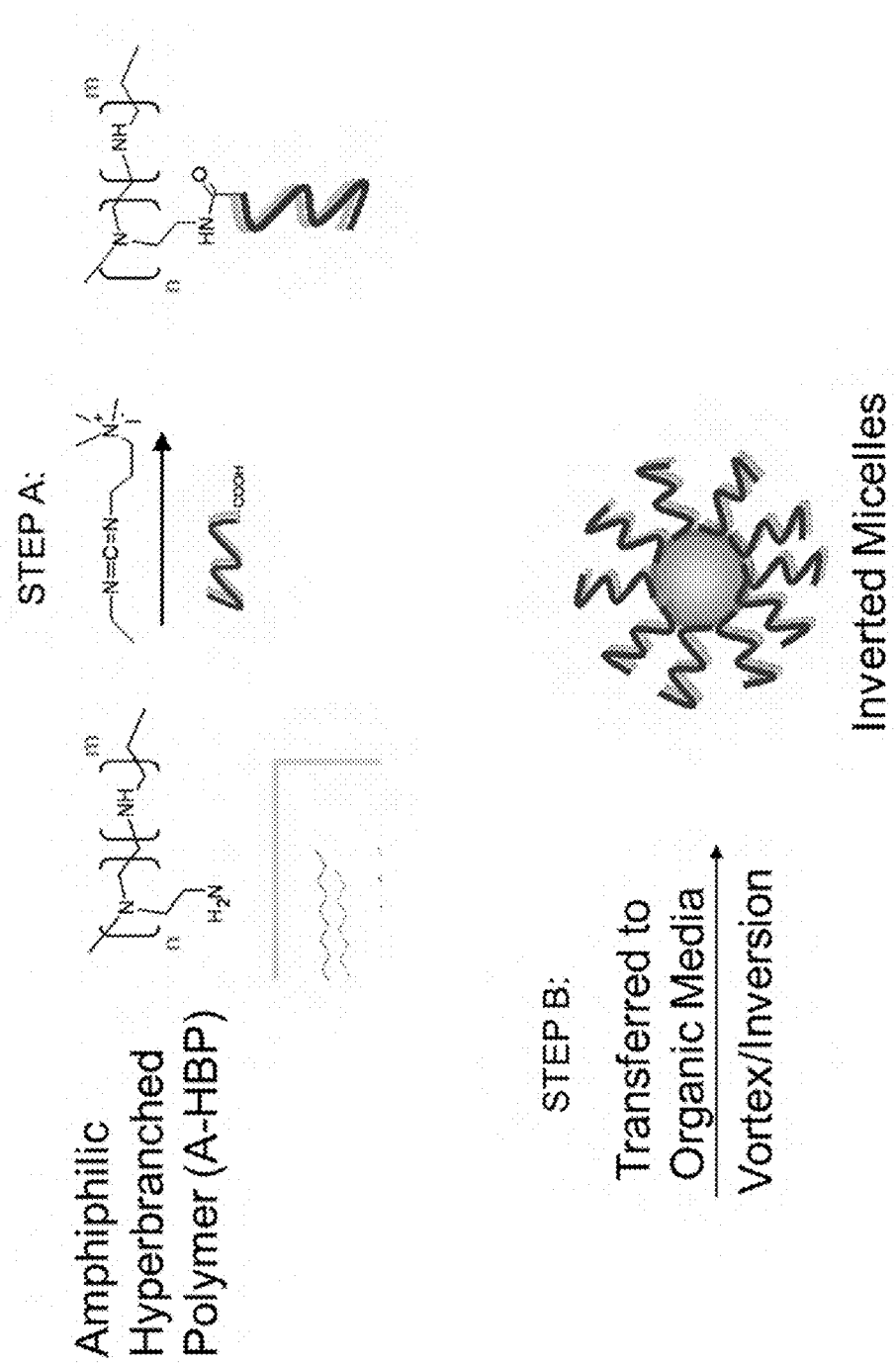
FIG. 2A-C depicts a schematic representation of nanoparticle preparation. (A) Depicts production of inverted micelles. Step A comprises the hydrophobic modification. (B) Depicts conversion of micelles into inverted nanoparticles. (C) Depicts cross-linking and dialysis steps. Step C comprises intra molecular chemical cross-linking.
Figure 2B:
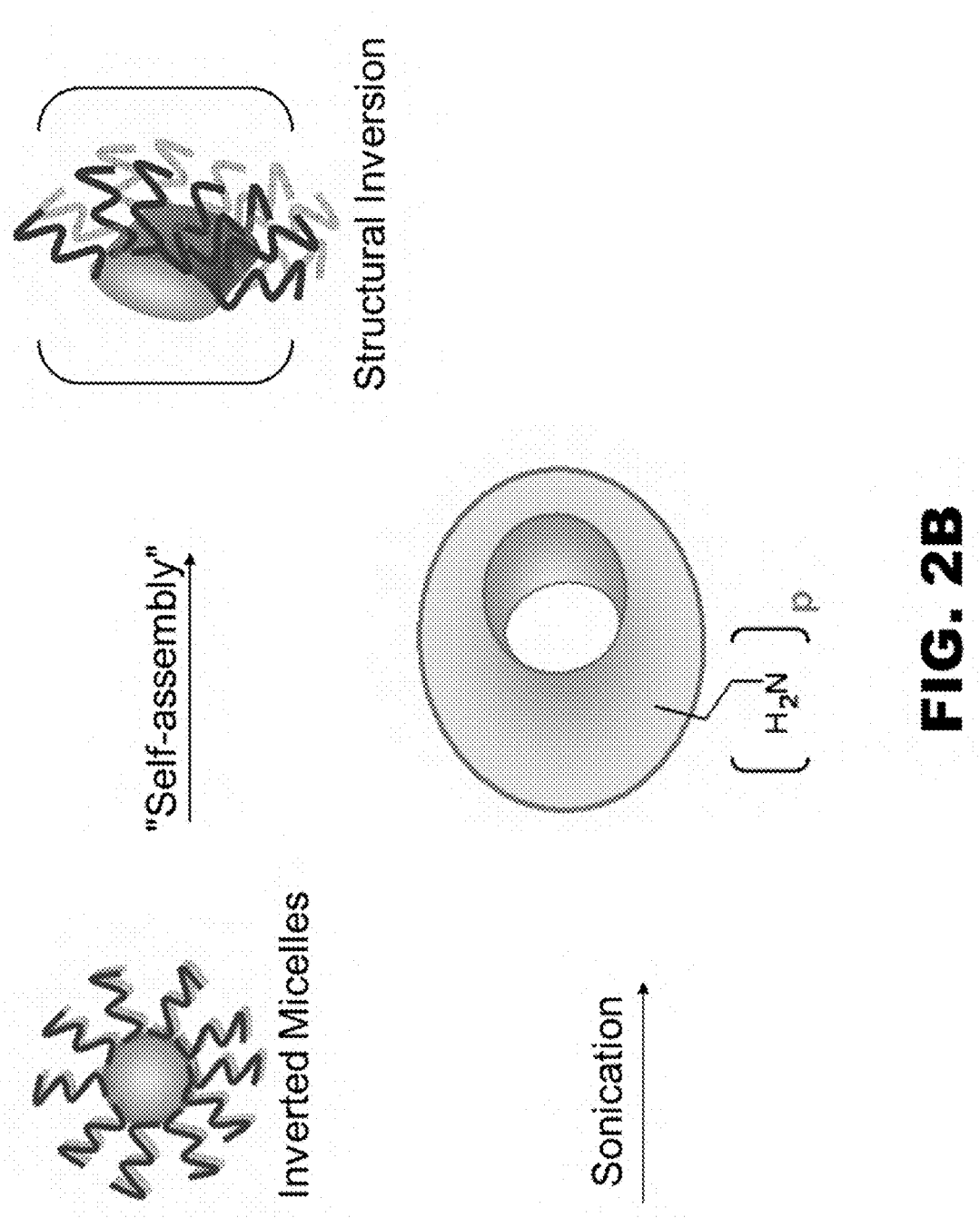
Figure 2C:
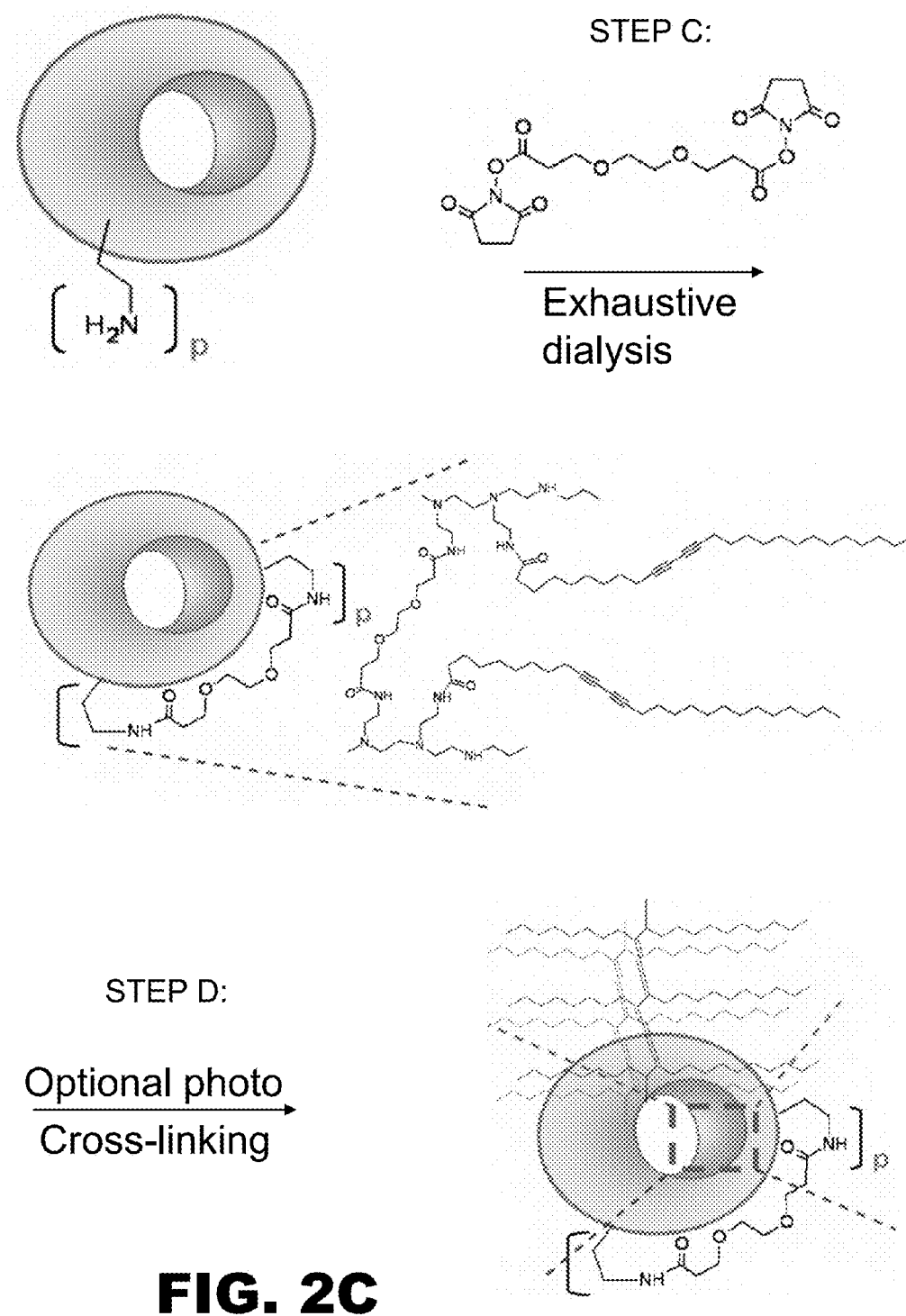
Figure 3:
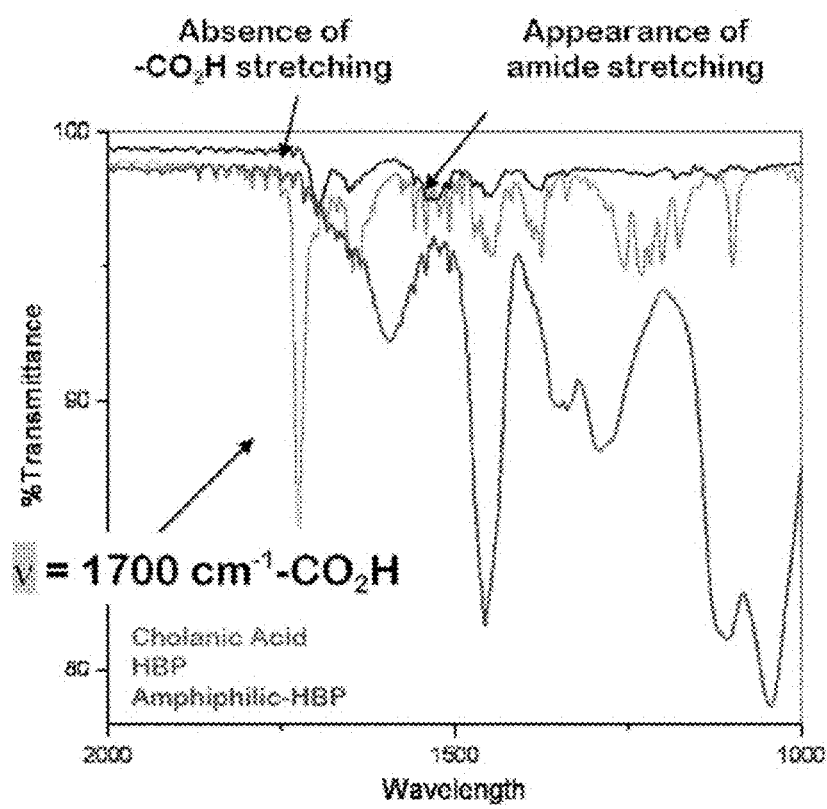
FIG. 3 depicts the monitoring of hydrophobic modification by the disappearance of stretching frequency of —$CO_2H$ (v=1700 $cm^{-1}$) and appearance of new amide peaks around v=1530 $cm^{-1}$.

Biconcave nanoparticles are a "theranostic" delivery system that can provide a constant delivery rate, target a specific location and simultaneously carry a contrast agent to image the target tissue (FIG. 1). A schematic representation of the preparation of nanoparticles is shown in FIG. 2. In short, hyperbranched or dendritic polymers were grafted with hydrophobic alkyl groups by covalent means. Fatty acids were activated with the carbodiimide EDAC (1-ethyl-3-(3-dimethylaminopropyl) carbodiimide, hydrochloride) followed by addition of the polymer to achieve greater than 50% functionalization of free primary amine groups. The hydrophobic modification was monitored by the disappearance of stretching frequency of —$CO_2H$ ($v=1700$ $cm^{-1}$) and appearance of new amide peaks around $v=1530$ $cm^{-1}$ (FIG. 3). The amphiphilic polymer assumed a 7-10 nm sized unimolecular inverted micellar structure in organic solvent after vortexing.

Water soluble guest compounds (e.g. FITC, ethyl orange, $Gd^{3+}$ DTPA, Mn(III)-porphyrin) were encapsulated within the polymer by gentle inversion mixing (1:1 v/v). This design allows chemical cross-linking of the surface and photo cross-linking of the shell to enhance stability and structural integrity of the nanoparticles.

Figure 4A:
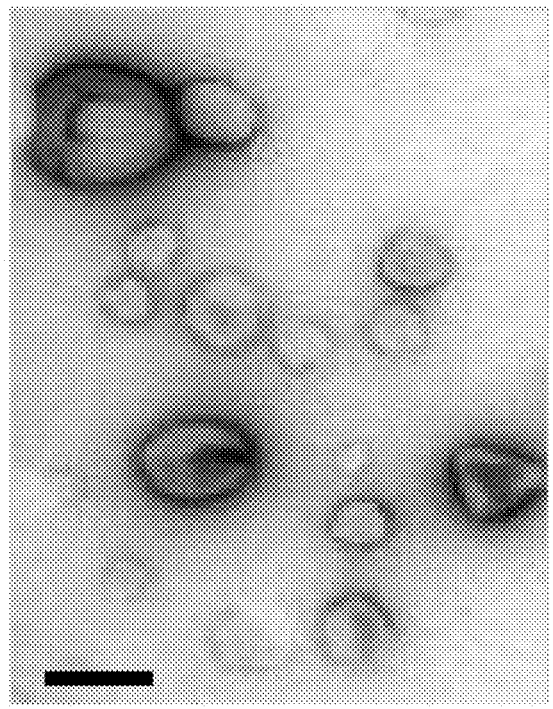
FIG. 4 depicts TEM of nanoparticles with (A) 40-66% nominal surface modification, and (B) 5-10% nominal surface modification.
Figure 4B:

The nanoparticles were chemically cross-linked on the surface by using short length bis-PEG-amine and, optionally, the membrane cross-linking may be carried out photochemically in a UV-cross linker (FIG. 2). In both cases, the nanoparticles were extensively dialyzed to remove unreacted small molecules or side products. Nominally, 40% of the surface primary amine functionalization is required to achieve the optimum hydrophobic character of the particles. With a polymer comprising less than 40% of surface conjugated fatty acids, the formation of bi-concaved disc shaped nanoparticles was not observed by TEM (FIG. 4).

Nanoparticle sizes, shape, and morphology were measured by TEM, DLS, and AFM.

Example 2

Evidence of Membrane Cross-Linking: Structure Variance with Temperature

Figure 5A:
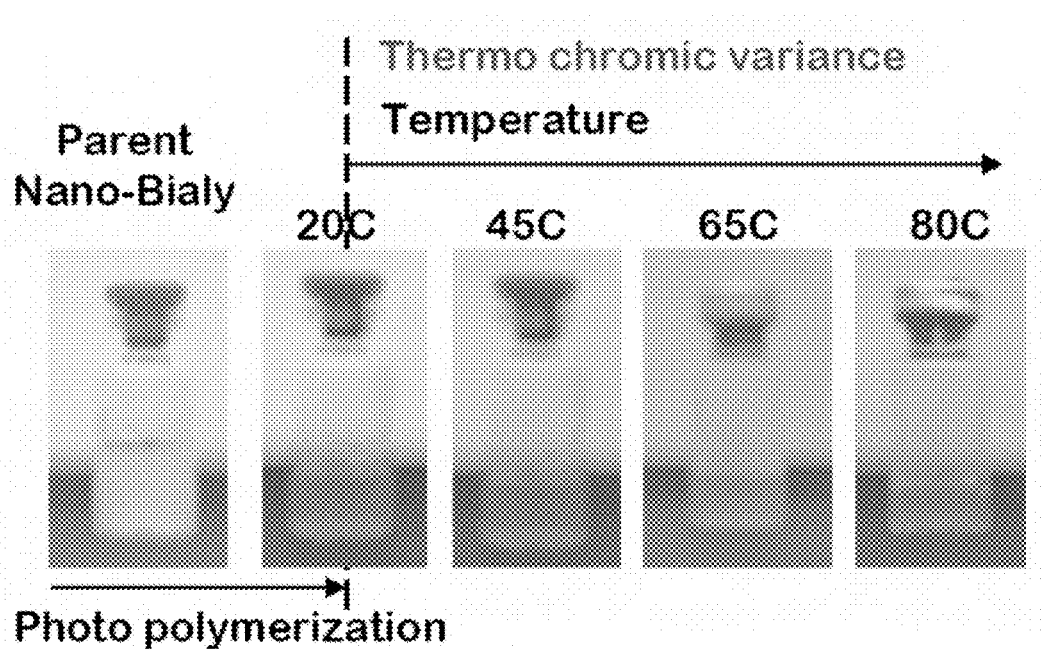
FIG. 5A-C depicts the schematic and evidence for membrane cross-linking. (A) Depicts thermochromic variance after photopolymerization of nanoparticles. (B) Depicts UV-vis evidence of membrane cross-linking. (C) Depicts a schematic of cross-linking reaction and following isomerization to produce the final butatriene system.
Figure 5B:
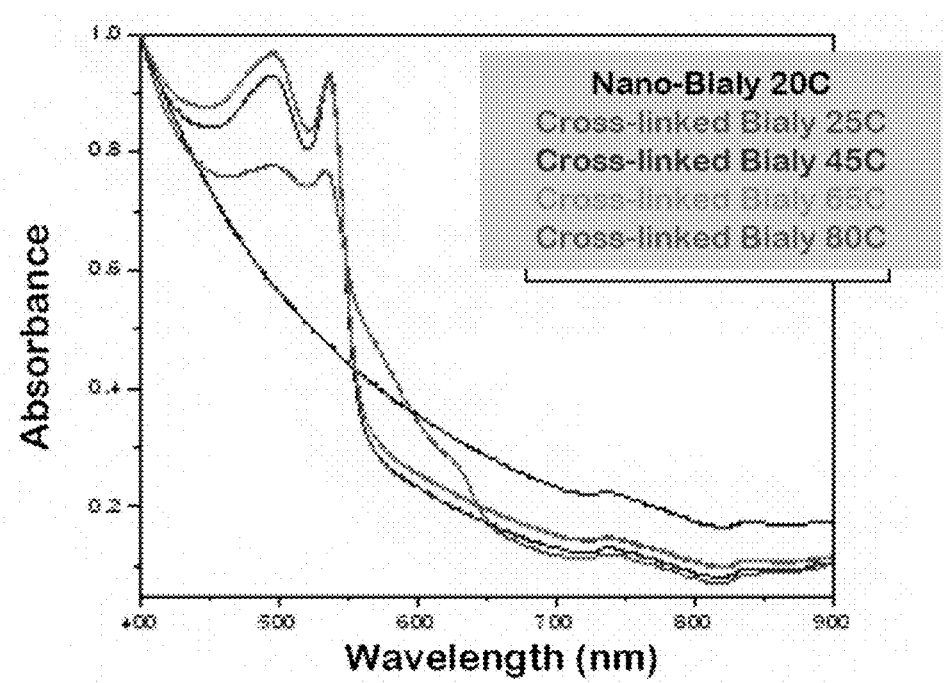
Figure 5C:
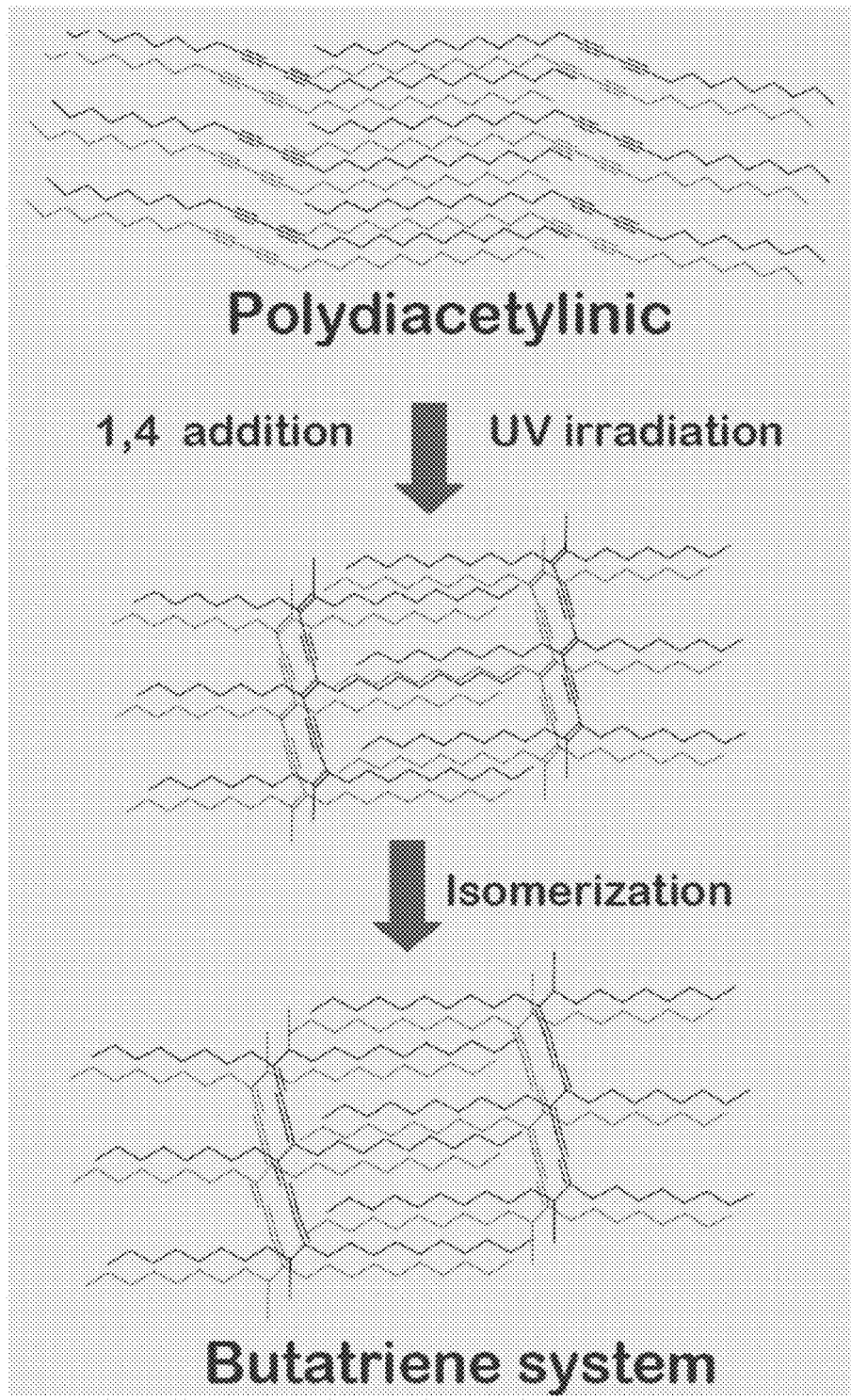

Membrane cross-linking and thermochromic variance could be visually observed (FIG. 5A) by UV-vis spectroscopy. The evidence of membrane photo cross-linking was observed from UV-vis studies (FIG. 5B). Polydiacetylinic bonds undergo intramolecular 1,4-addition upon UV exposure at 254 nm to form ene-yne linkages. The particles were typically irradiated for 0.5 hr and allowed to come to room temperature before storage at between 2 and 8° C. The ene-yne bonds were found to isomerize to a butatriene system with increases in temperature (FIG. 5C).

Example 3

Preparation of Functionalized Nanoparticles

Biotinylated and targeted nanoparticles were produced by pre- or post-self-assembly functionalization strategies for in vitro targeted drug delivery evaluation, but direct coupling is required for homing ligands for specific targets. The biotins can be incorporated by using biotin-cap-PE by pre-assembly means. A direct coupling method can also be followed and NHS-biotin (EZ-LINK Biotin®) is used to conjugate biotin onto the surface-available free amine groups of the nanoparticles. Following a similar technique, nanoparticles can be efficiently labeled with dyes (e.g. Rhodamine-B, NBD, FITC, and others). The pegylation of the particles was achieved by using PEG2000-DSPE. It was observed that at least a nominal 50% surface coverage was required to coat the entire surface of these particles. Particle sizing experiments confirm that the particle diameters remained comparable even after the functionalization (Table 1).

TABLE 1

| Particle | DLS ($D_{av}$) nm | Zeta mV |
| --- | --- | --- |
| Biotinylated | 165 +/− 10 | 15 +/− 5 |
| Rhodamine-B labeled | 178 +/− 24 | 16 +/− 6 |
| 10% PEG-lipid loaded | 185 +/− 24 | 29 +/− 10 |
| 50% PEG-lipid loaded | 219 +/− 24 | −16 +/− 6 |

Figure 6A:
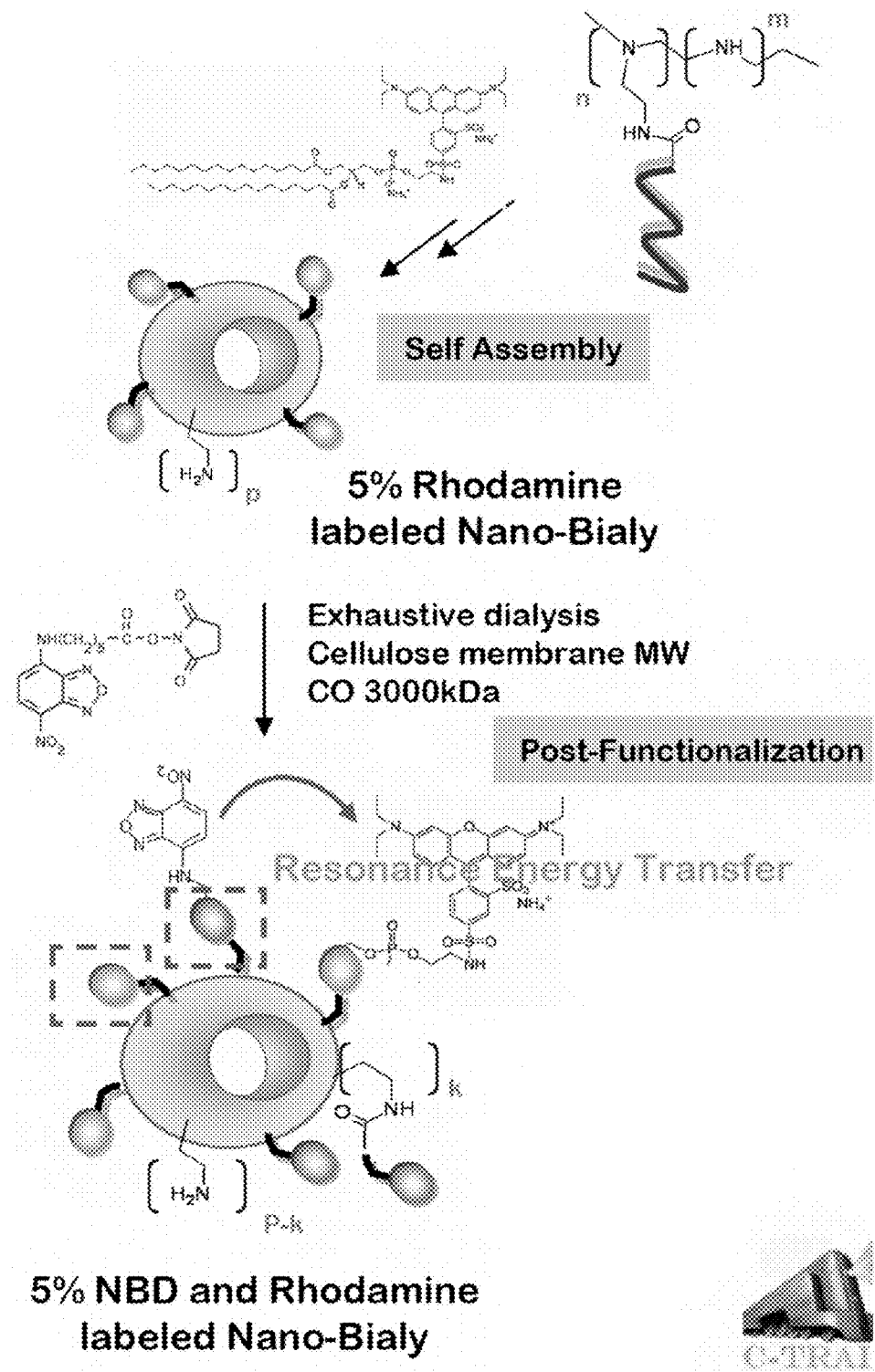
FIG. 6A-B depicts the confirmation of the location of ligands by FRET. (A) Depicts a schematic describing the assembly of doubly-labeled nanoparticles for FRET. (B) Depicts fluorescent energy transfer in the doubly-labeled particles (red curve) compared to the absence of fluorescence energy transfer in the control rhodamine-labeled particles.
Figure 6B:
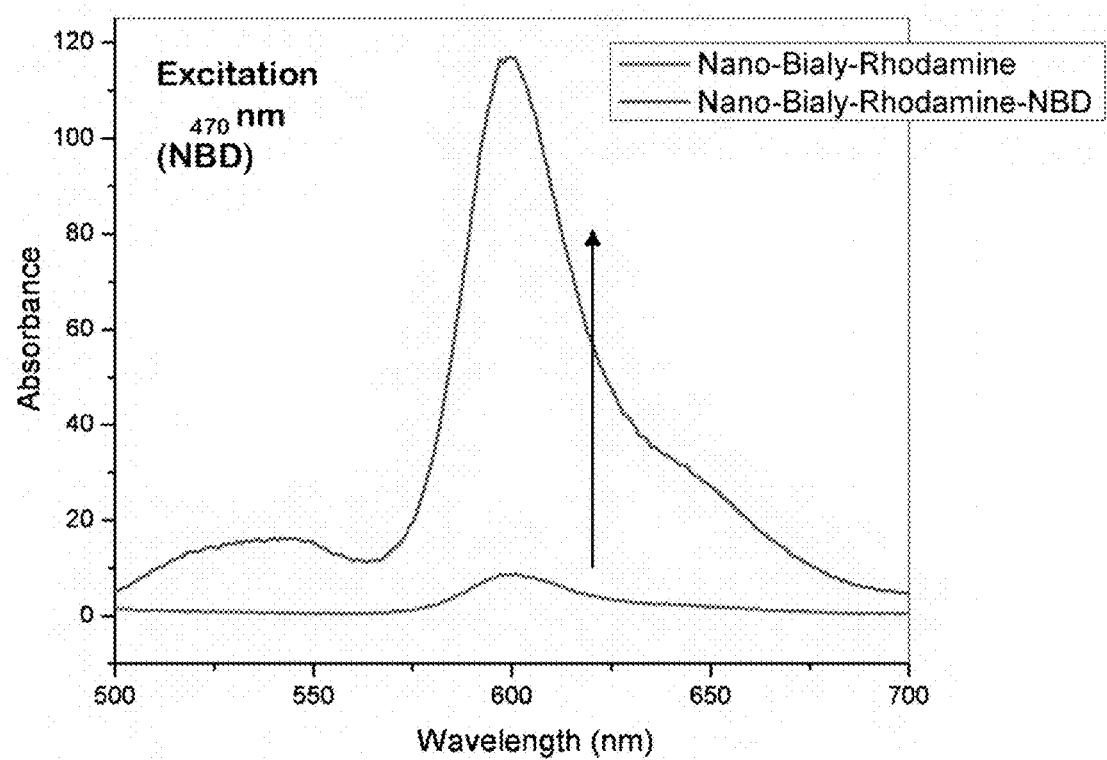

Confirmation of the location of nanoparticles functionalized with pre- and post-assembly dyes was measured by fluorescence resonance energy transfer (FRET). In short, 5% rhodamine labeled nanoparticles were assembled, and post-functionalized with nitrobenzoxazide (NBD) dye (FIG. 6A). FRET was measured for the double-labeled particles and the control rhodamine-labeled particles (FIG. 6B).

Example 4

In Vitro Bioavailability Studies of Surface Bound Biotin

Figure 7A:
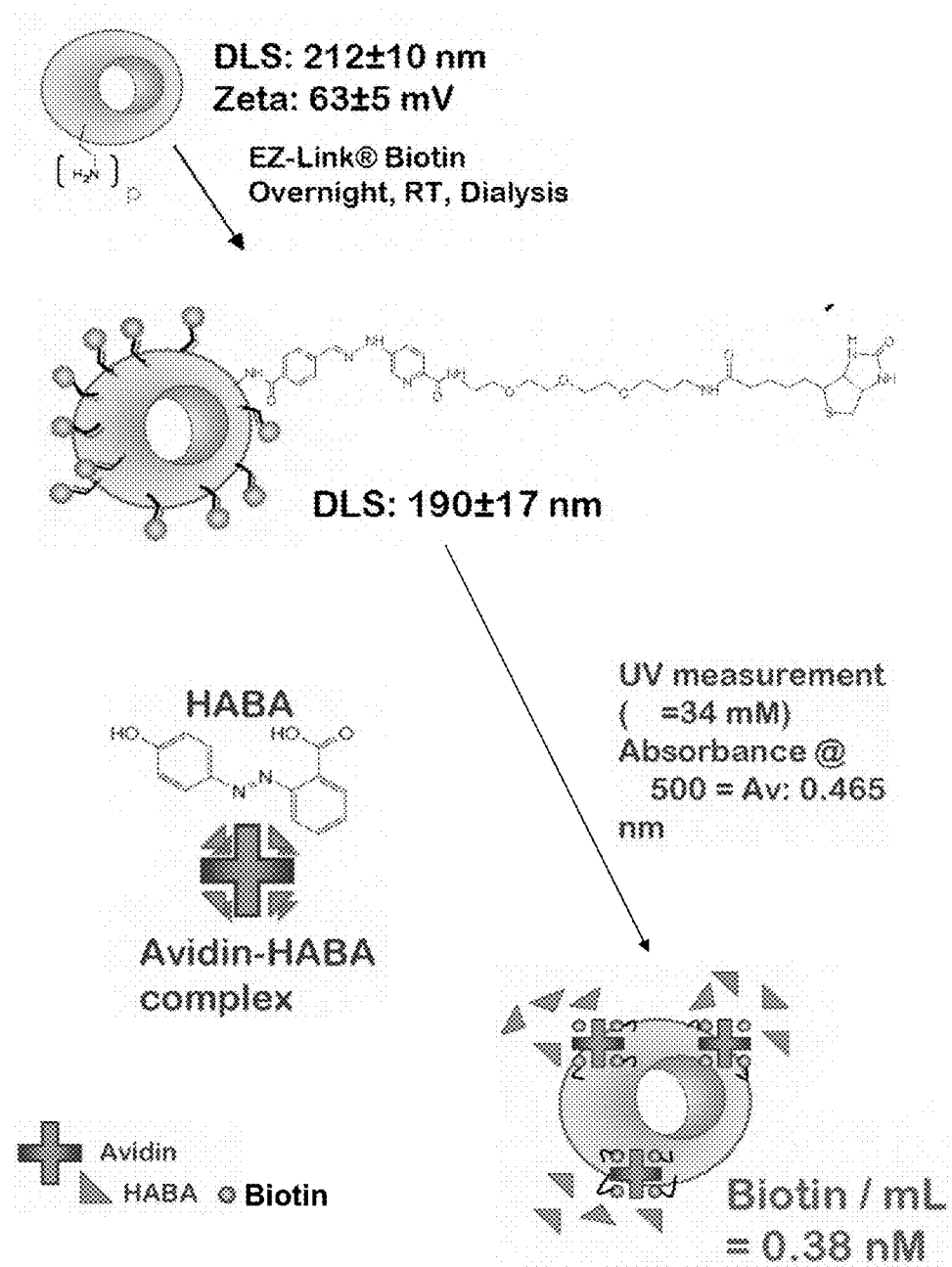
FIG. 7A-B depicts the HABA displacement assay used to evaluate bioavailability of the surface bound biotins linked to nanoparticles after assembly (A), or incorporated into nanoparticles during assembly (B).
Figure 7B:
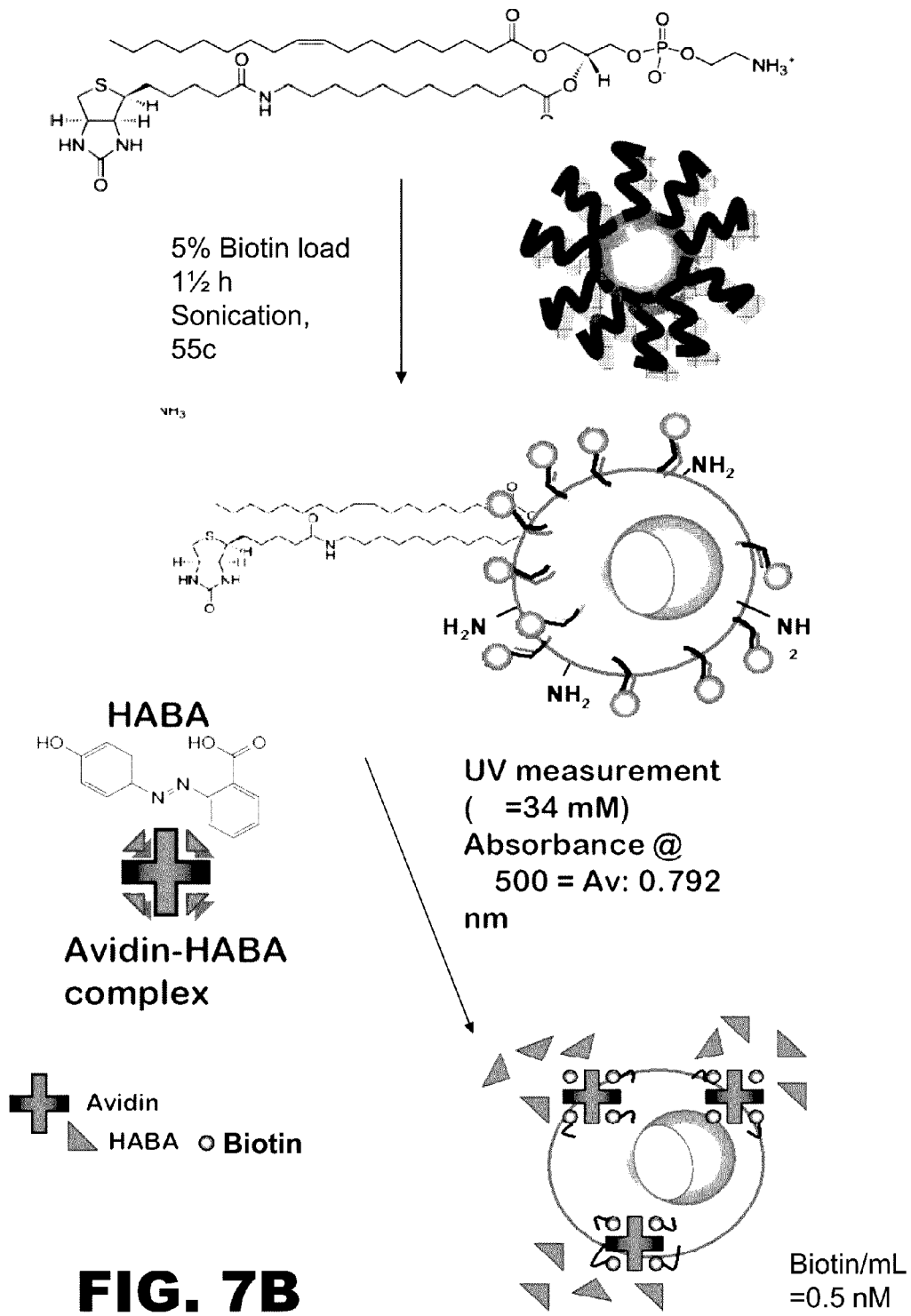

Surface bound biotin was found to be bio-available by in vitro avidin/HABA competitive ligand binding assays (FIG. 7). The HABA dye (4'-hydroxyazobenzene-2-carboxylic acid) binds to avidin to produce a yellow-orange colored complex, which absorbs at 500 nm. Biotin displaces the HABA dye and causes the absorbance to decrease. An average of 0.38 nM and 0.5 nM biotin/mL was found to be bioavailable for biotinylated nanoparticles prepared by pre- or post-self-assembly techniques, respectively.

Example 5

Preparation and Characterization of Biotinylated, Manganese(III)-Labeled Nanoparticles Manganese(III)-labeled nanoparticles are a potential targeted magnetic resonance (MR) theranostic nanoparticle. The nanoparticles were produced by molecular self-assembly of amphiphilic branched polyethylenimine. The nanoparticles have a bi-concaved disc shape, tunable particle size, and low polydispersity. The bi-concaved disc shape affords increased stability and presents kinetically stable, porphyrin coupled Mn(III) complexes directly to the surrounding water.

Figure 8:
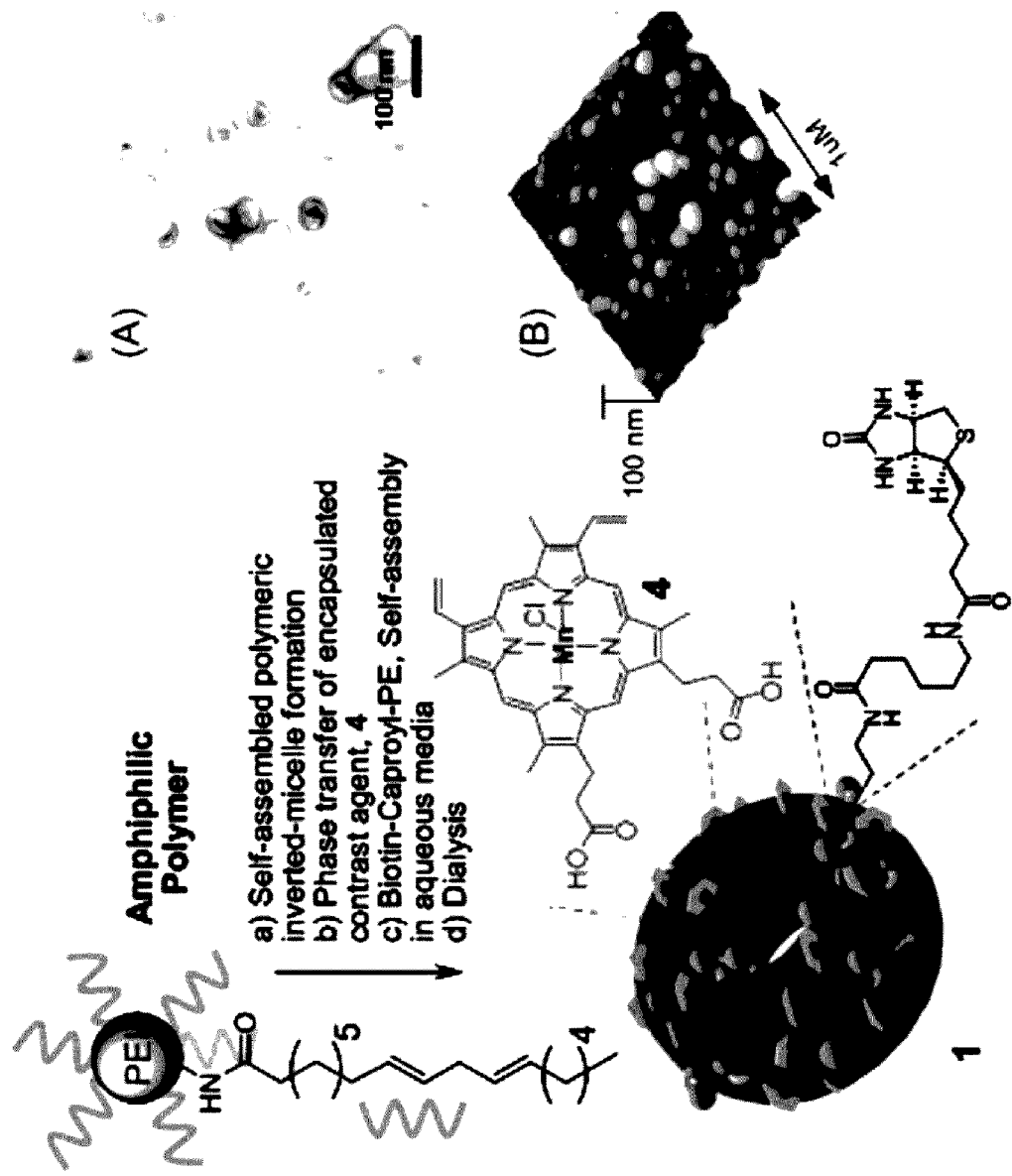
FIG. 8A-B depicts the preparation of biotinylated-manganese(III)-labeled nanoparticle, and (A) transmission electron microscope image of nanoparticles drop-deposited over nickel grid, (B) atomic force microscope image of nanoparticles. Conditions for the steps listed in the figure are as follows: (a) anhydrous chloroform, gentle vortexing, room temp; (b) aqueous solution of manganese(III)-protoporphyrin chloride (Mn-PPC, 4), inversion, room temp, filter using short bed of sodium sulfate and cotton; (c) biotin-caproyl- PE, filter mixed organic solution using cotton bed, 0.2 µM water, vortex, gently evaporation of chloroform at 45° C., 420 mbar, 0.2 uM water, sonic bath, 50° C., ½ h, dialysis (2 kDa MWCO cellulose membrane) against water.

In a typical synthesis depicted in FIG. 8, commercially available branched polyethylenimines (MW 10 kDa) were hydrophobically modified (nominal 55% conjugation of the 1°amine) with linoleic acid by activating the carboxylic acid groups with 1-(3'-dimethylaminopropyl)-3-ethylcarbodiimide methiodide (1.2 equiv) and allowing the reaction overnight at ambient temperature. Supramolecular self-assembly of the amphiphilic polymer in anhydrous chloroform, assumes inverted micellar structures that are able to transfer a water soluble new candidate contrast agent Mn(III)-protoporphyrin chloride (Mn-PPC) into chloroform. Synergistic self-assembly of the agent (3) alone or in presence of biotin-caproyl-DSPE (5 w/w % of total amphiphiles), presumably leads to the bilayer structure of nanoparticles. The entrapment of manganese within the inverted micelles at the surface of the nanoparticles affords accessibility to water and eliminates detrimental interactions with surface homing ligands or surrounding plasma proteins. Nonbiotinylated (Mn(III)-labeled) and biotinylated nanoparticles without metal were produced as controls.

In the examples that follow, Mn(III)-labeled biotinylated nanoparticles and control unbiotinylated Mn(III)-labeled nanoparticles and unbiotinylated, unlabeled nanoparticles are prepared, and characterized. Their ability to target fibrin clots and deliver therapeutic compounds is also assessed.

Example 6

Typical Procedure for the Preparation of Biotinylated-Mn(III)-Labeled Nanoparticles Unless otherwise listed, all solvents and reagents were purchased from Aldrich Chemical Co. (St. Louis, Mo.) and used as received. Anhydrous chloroform was purchased from Aldrich Chemical Co. and distilled over calcium hydride prior to use. Branched polyethylenimine was purchased from Alfa Aesar. Biotinylated dipalmitoylphosphatidylethanolamine was purchased from Avanti Polar Lipids, Inc. Manganese protoporphyrin chloride was purchased from Frontier Scientific, Inc. Argon and Nitrogen (UHP, 99.99%) was used for storage of materials. Spectra/Por membrane (MWCO: 2 000 Da) used for dialysis was obtained from Spectrum Medical Industries, Inc. (Laguna Hills, Calif.).

Procedure

To a stirred solution of linoleic acid (3.05 g) in anhydrous chloroform (10 mL), was added a solution of 1(3'dimethyl-aminopropyl)-3-ethylcarbodiimide methiodide (1.5 equiv. of acid) in chloroform (5 mL). The reaction vessel was protected from light and moisture using a calcium chloride drying tube and the mixture was allowed to react for ½ at room temperature. The color of the mixture turned yellow and to this, a solution of commercially available branched polyethylenimines (MW=10 000 Da, L=40%, D=27%, T=33%) (0.5 g, 0.55 equiv. of primary amine residues activation) in anhydrous chloroform (5 mL) was added dropwise. The solution was allowed to stir overnight at ambient temperature. The solvent was removed under reduced pressure and amphiphilic polymer was purified followed by a reported procedure (Chen, Y. et. al. Macromolecules 2005, 38, 227-229.). These amphiphilic polymers (26 mg) assume an inverted micellar structure in organic solvent (anhydrous chloroform) after gentle vortexing for 2 min. Manganese protoporphyrin chloride (Mn(III)PPC) was dissolved in water (a slightly basic pH was necessary to ensure a clear aqueous suspension) and was added to the inverted micelle solution of the amphiphilic polymer. The gentle inversion mixing of the biphasic system (1:1 v/v) allowed the transfer of the contrast agent from the aqueous to the organic phase. The organic phase (~5 mL of chloroform layer) was separated out from the aqueous part and dried by passing through a bed of sodium sulfate and cotton. Biotinylated dipalmitoylphosphatidylethanolamine (Avanti Polar Lipids, Inc.) was weighed separately (5 w/w %), dissolved in anhydrous chloroform, dried ($Na_2SO_4$) and mixed well with the organic phase. Excess of anhydrous chloroform (30 mL) was added to the organic phase and was taken in a 50 mL, long necked test tube. To this, 5 mL of nanopure water (0.2 μM) was injected and gently vortexed for a few minutes. The chloroform was then slowly evaporated under reduced pressure at 45° C. for 30-45 min, maintaining the pressure at 420-440 mbar. To this, an additional 5 mL of nanopure water (0.2 μM) was injected. The dispersion was sonicated in a Branson ultra-sonic bath for ½ h (until a clear dispersion formed) maintaining the bath temperature at 50° C.

Results

Figure 9:
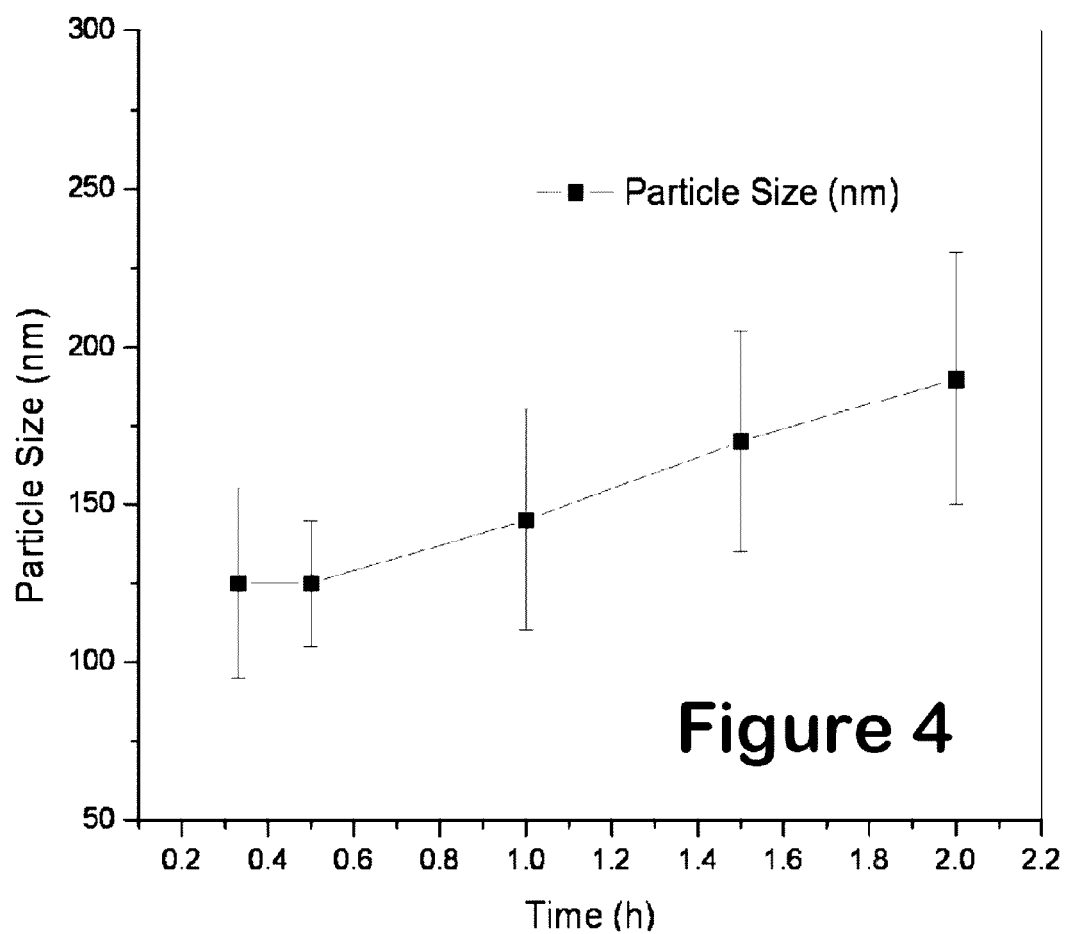
FIG. 9 depicts the variation of particle size of nanoparticles with sonication time.
Figure 10:
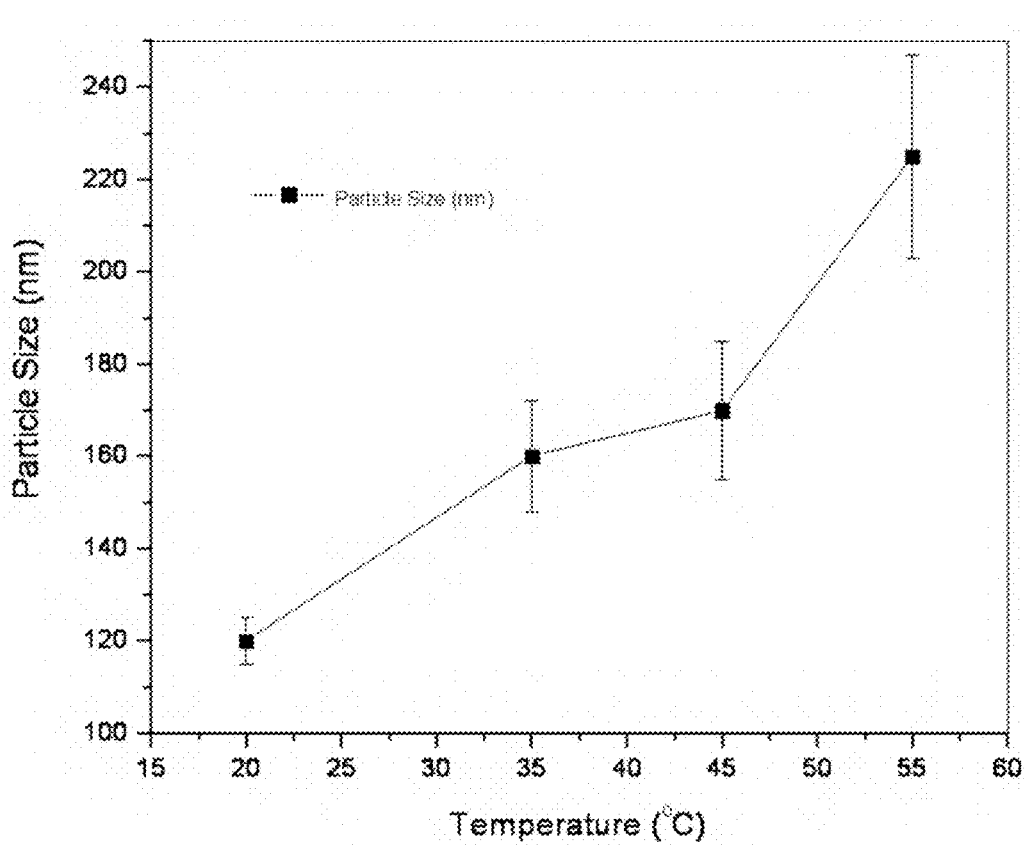
FIG. 10 depicts the dependence of particle size on temperature during the self-assembly protocol.

It was observed that a bath sonication time of more than 2 h, >1 μM sized particle were formed (FIG. 9). The particle size can be tuned by changing the temperature at the time of the self-assembly (FIG. 10). The chemistry was conducted in aqueous solution and the manganese(III)-labeled nanoparticles were purified by dialysis through 2 000 Da molecular weight cutoff (MWCO) cellulose membrane.

Figure 11:
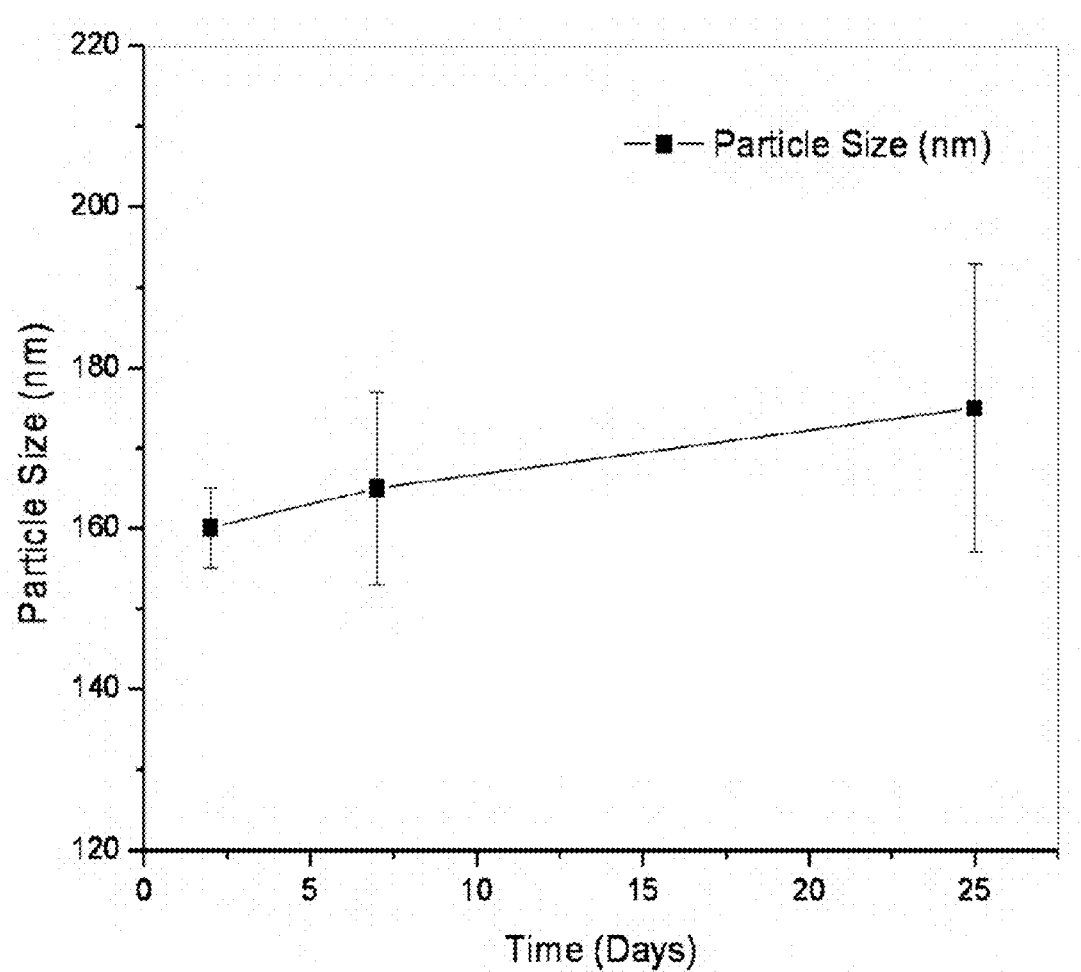
FIG. 11 depicts the variation of particle size of biotinylated, manganese(III)-labeled nanoparticles with time.

The nanoparticles were stored at 4° C. protected from light. Hydrodynamic diameters were recorded over a period of 30 days to study the shelf life of these particles. If stored at 4° C. protected from light, the nanoparticles were found to be stable over months (FIG. 11).

Figure 12:
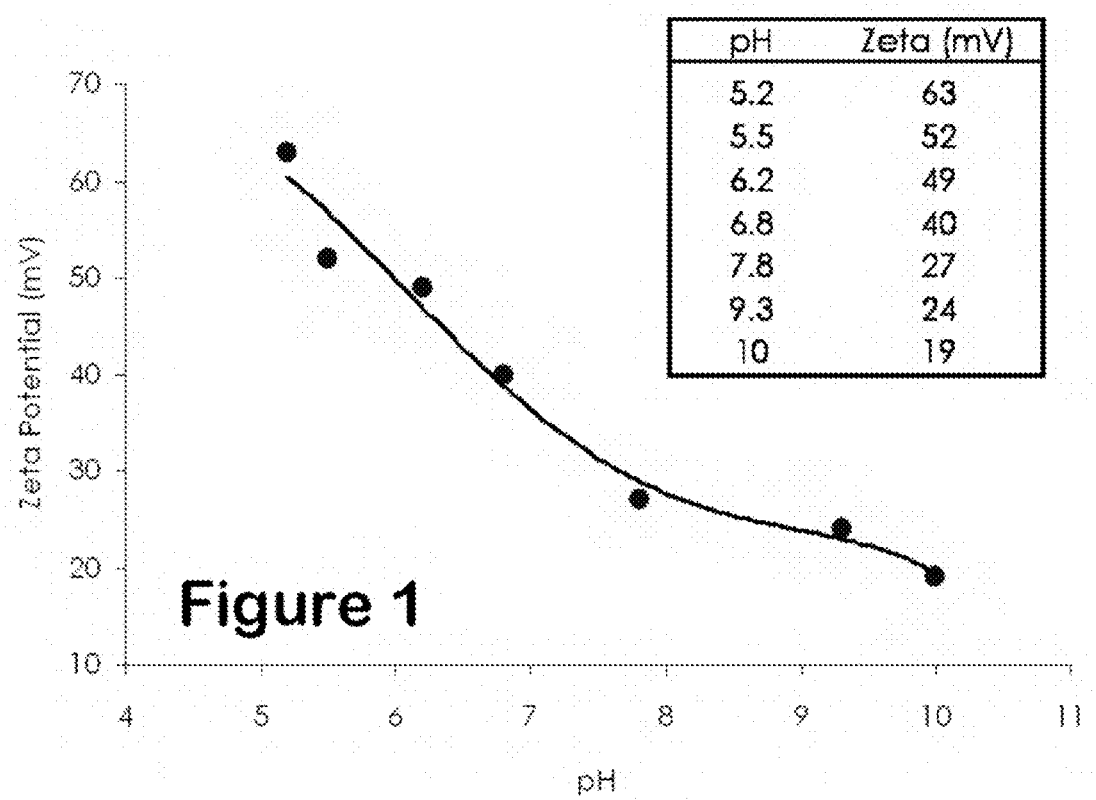
FIG. 12 depicts the zeta potential as a function of pH.
Figure 13A:
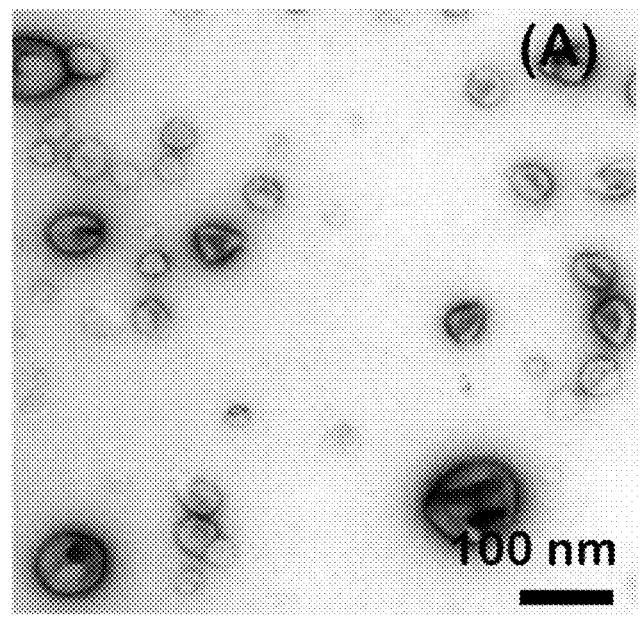
FIG. 13A-E depicts microscopy images of particles of the disclosure. (A-B) depict transmission electron microscopy images of biotinylated manganese(III)-labeled nanoparticles and non-biotinylated manganese(III)-labeled nanoparticles, respectively. The samples were prepared by addition of 1% aqueous uranyl acetate solution, followed by drop deposition from the aqueous solution upon a carbon/formvar-coated nickel grid and allowing them to dry freely in air. (C-E) Depict tapping-mode atomic force microscope images of biotinylated manganese(III)-labeled nanoparticles, non-biotinylated manganese(III)-labeled nanoparticles and non-biotinylated unlabeled nanoparticles, respectively.
Figure 13B:
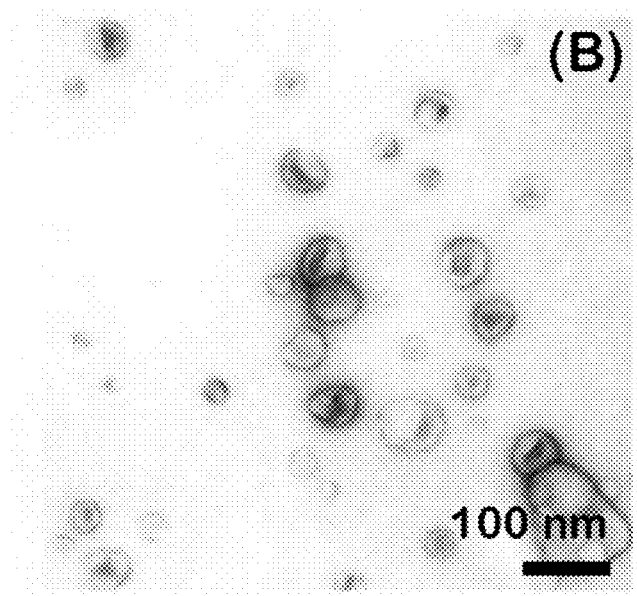
Figure 13C:
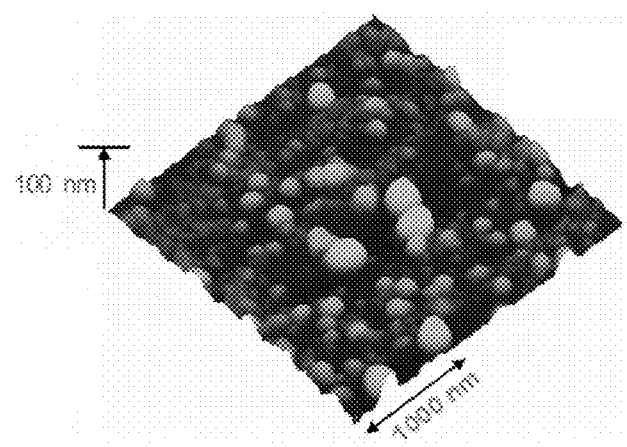
Figure 13D:
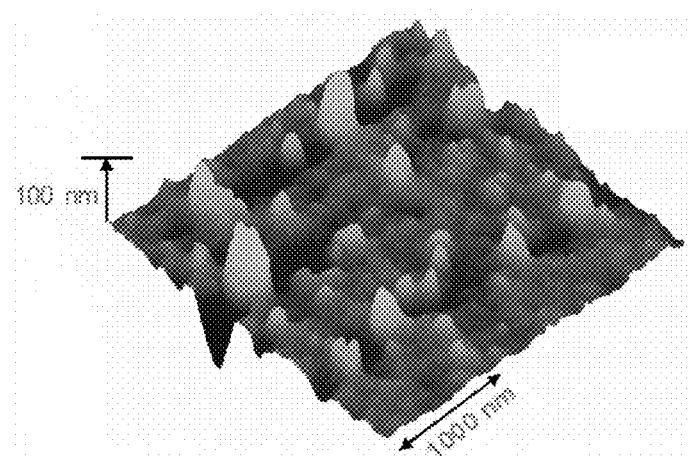
Figure 13E:
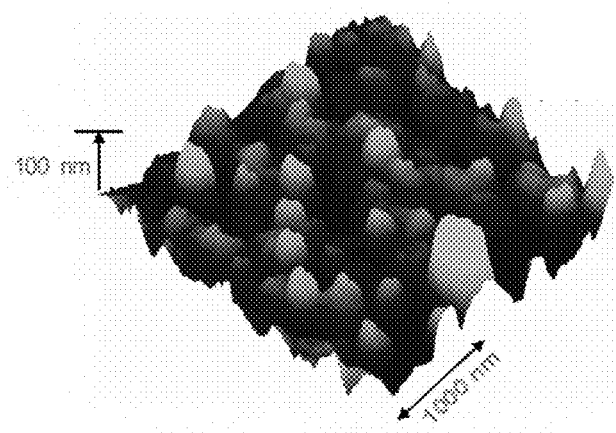

An isoelectric point for the nanoparticles was not found with a pH range of 5-10 from electrophoretic light scattering measurements, and thus it was concluded that the colloidal system seems to be stable in that range (preferably at lower pH, FIG. 12).

Example 7

Typical Procedure for the Preparation of Control Biotinylated-Nanoparticles Not Labeled with Manganese(III)

Typically, as described in Example 2 above, amphiphilic polymers (approx. 25 mg) in organic solvent (anhydrous chloroform) is gently vortexed for 2 min. Biotinylated dipalmitoylphosphatidylethanolamine (Avanti Polar Lipids, Inc.) was weighed separately (5 w/w %), dissolved in anhydrous chloroform and mixed well with the organic phase. The mixed organic phase (~5 mL of chloroform layer) was dried by passing through a bed of sodium sulfate and cotton. Excess of anhydrous chloroform (30 mL) was added to the organic phase and was taken in a 50 mL, long necked test tube. To this, 5 mL of nanopure water (0.2 μM) was injected and gently vortexed for few minutes. The chloroform was then slowly evaporated under reduced pressure at 45° C. for 30-45 min, maintaining the pressure at 420-440 mbar. To this, an additional 5 mL of nanopure water (0.2 μM) was injected. The dispersion was sonicated in a Branson ultra sonic bath for ½ h (until a clear dispersion formed) maintaining the bath temperature at 50° C. The biotinylated nanoparticles thus formed, were purified by dialysis through 2 000 Da MWCO cellulose membrane.

Example 8

Typical Procedure for the Preparation of the Manganese(III)-Labeled Non-Biotinylated Control Nanoparticles Typically, as described in Example 2 above, amphiphilic polymers (approx. 25 mg) in organic solvent (anhydrous chloroform) was gently vortexed for 2 min. Manganese protoporphyrin chloride (Mn(III)PPC) was dissolved in water (a slightly basic pH was necessary to ensure a clear aqueous suspension) and was added to the inverted micelle solution of the amphiphilic polymer. The gentle inversion mixing of the biphasic system (1:1 v/v) allowed the transfer of the contrast agent from the aqueous to the organic phase. The organic phase (~5 mL of chloroform layer) was separated out from the aqueous part and dried by passing through a bed of sodium sulfate and cotton. The mixed organic phase (~5 mL of chloroform layer) was dried by passing through a bed of sodium sulfate and cotton. Excess of anhydrous chloroform (30 mL) was added to the organic phase and was taken in a 50 mL, long necked test tube. To this, 5 mL of nanopure water (0.2 μM) was injected and gently vortexed for a few minutes. The chloroform was then slowly evaporated under reduced pressure at 45° C. for 30-45 min, maintaining the pressure at 420-440 mbar. To this, an additional 5 mL of nanopure water (0.2 μM) was injected. The dispersion was sonicated in a Branson ultra sonic bath for ½ h (until a clear dispersion formed) maintaining the bath temperature at 50° C. The biotinylated nanoparticles thus formed, were purified by dialysis through 2 000 Da MWCO cellulose membrane Example 9

Characterization of Nanoparticles

Dynamic Light Scattering Measurements

Hydrodynamic diameter distribution and distribution averages for the nanoparticles in aqueous solutions were determined by dynamic light scattering. Hydrodynamic diameters were determined using a Brookhaven Instrument Co. (Holtsville, N.Y.) Model Zeta Plus particle size analyzer. Measurements were made following dialysis (MWCO 2 kDa dialysis tubing, Spectrum Laboratories, Rancho Dominguez, Calif.) of nanoparticles solutions into deionized water (0.2 μM). Nanoparticles were dialyzed into water prior to analysis. Scattered light was collected at a fixed angle of 90°. A photomultiplier aperture of 400 mm was used, and the incident laser power was adjusted to obtain a photon counting rate between 200 and 300 kcps. Only measurements for which the measured and calculated baselines of the intensity autocorrelation function agreed to within +0.1% was used to calculate nanoparticle hydrodynamic diameter values. All determinations were made in multiples of five consecutive measurements.

Atomic Force Microscopy Measurements.

Digital Instruments Dimension 3000 series atomic force microscope (AFM) (Calibration date August 2007) and standard Veeco tapping mode silicon probes w/Ptlr coating was used for scanning the samples. In a typical methodology, aqueous suspensions of nanoparticles samples were dried in class 10000-clean room on clean glass slide for 3 h. Once dried, samples were placed on AFM and scanned. Pertinent scanning parameters were as follows: Resonant frequency (probe): 6080 kHz; Tip velocity: (4 um/s for 2 um), (15 um/s for 5 um), (30 um/s for 10 um) Aspect ratio: 1 to 1; Lift height: 20 nm; Resolution: 512 samples/line, 256 lines. The average particle height ($H_{av}$) values and standard deviations were generated from the analyses of a minimum of 100 particles from three micrographs.

Transmission Electron Microscopy Measurements

Glow discharged carbon/formvar coated nickel grids were floated on a drop of sample for 2 mins. Grids were blotted, rinsed quickly in water, and stained in 1% aqueous uranyl acetate for 1 min. Samples were blotted, air dried, and viewed on a Zeiss 902 Electron Microscope, and recorded with Kodak E.M. film. Micrographs were collected at 100,000× magnification. The number-average particle diameter ($D_{ah}$) values and standard deviations were generated from the analyses of a minimum of 100 particles from three micrographs.

UV-Visible Spectroscopy

Absorption measurements were made with a Shimadzu UV1601 P/N 20667001 spectrophotometer using ShimadzuUV probe 2.21 software.

Inductively Coupled Plasma-Optical Emission Spectroscopy

After imaging, the manganese content of each phantom was analyzed by inductively coupled plasma-optical emission spectroscopy (ICP-OES, SOP7190, Rev 2) conducted at the Bodycote, West Coast Analytical Service (WCAS), Santa Fe Springs, Calif. Briefly, the samples were analyzed by a Leeman Labs Direct Reading Echelle ICP-OES, or DRE instrument which was designed to handle sub-ppm to percent level metal concentrations.

Results

Hydrodynamic particle size for the biotinylated without metal (180+/−9 nm), biotinylated-Mn(III)-labeled (190+/−5 nm) and nonbiotinylated-Mn(III) nanoparticles (200+/−12 nm) were similar with a narrow distribution (polydispersity 0.18+/−0.01, 0.26+/−0.01, and 0.17+/−0.01, respectively). In the anhydrous state, tapping mode atomic force microscopy (AFM) and transmission electron microscopy (TEM) revealed decreased particle height ($H_{av}$=60+/−15) and diameter ($D_{av}$=95+/−26) values (FIG. 13). Characteristic changes in UV absorbance between 370 and 550 nm confirmed inclusion of the Mn(III)-porphyrin. Manganese content was 25.6+/−03 μg/mL by inductively coupled plasma atomic emission spectroscopy (ICP-OES), that is, 165 000 Mn(III) per nanoparticle.

Example 10

Magnetic Resonance Imaging

Instruments and Methods

Relaxivity measurements were obtained for the nanoparticles at both 1.5 T and 3.0 T using spin-echo (SE) and inversion recovery (IR) techniques. Mn(III)labeled and control nanoparticles were diluted with distilled deionized water in ratios of 1:0, 1:1, 1:4, 1:8, and 1:10. All images were acquired on a 1.5 T and 3.0 T clinical scanner (Achieva; Philips Medical Systems, Best, Netherlands) with a quadrature birdcage receiver coil. An image resolution of 0.78 mm×0.78 mm×5 mm was used. Test tubes with 1 mL of nanoparticle suspension (concentration ranging from 1:0 to 1:10) were placed vertically in a clinical MR scanner and imaged in cross section (to reduce through plane partial volume effects). T1 measurements were calculated from the real component of the images collected with an IR MRI pulse sequence. T2 was calculated from multi echo SE images with a range of echo times (TE, ΔTE=15 ms; number echoes=30) using the technique described by Look and Locker (Look D C, Locker D R. Time saving in measurement of NMR and EPR relaxation times. *Rev. Sci. Instrum.* 1970; 41(2):621-627.), following a 180 degree inversion pulse, the magnetization recovery was sampled 76 times every 40 ms with a gradient echo imaging technique using a flip angle of 6 degrees. The time between successive inversion pulses was 6 seconds. The resulting images were analyzed using custom software, which calculates relaxation rates on a pixel-by-pixel basis. The relaxivities (i.e., r1 and r2) were calculated from the slope of the linear least squares regression of relaxation rate vs. Mn(III), i.e. ion relaxivity, or nanoparticle, i.e. particle relaxivity, concentrations and are reported in units of $(s \cdot mM)^{-1}$. Parameters were estimated as mean % std dev within regions of interest drawn within the test tubes of various concentrations.

Nanoparticle Phantoms

Five nanoparticle test phantoms were prepared in snap cap tubes. Selected volumes (1:0, 1:1, 1:4, 1:8, and 1:10) of the nanoparticle samples were added to five of the six phantoms and diluted by adding deionized water. For target specific imaging, clots were imaged at 3.0 T (TE=9.6 ms; TR=500 ms) using 3D T1-weighted TSE and a reconstructed pixel dimension was 0.38 mm×0.38 mm×1 mm slice thickness.

Human Plasma Clot Phantoms

Figure 14:
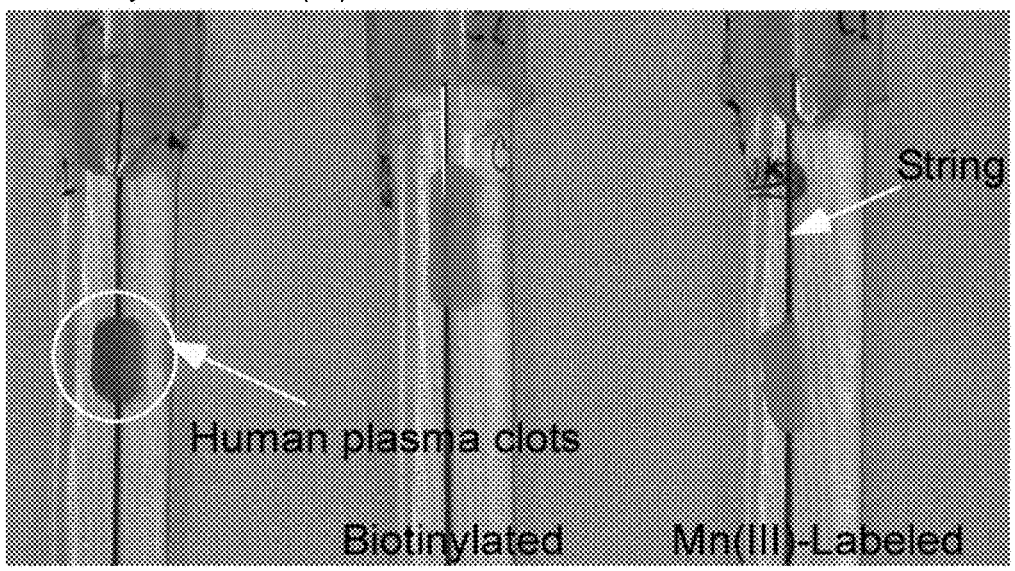
FIG. 14 depicts plasma clot phantoms targeted with biotinylated manganese(III)-labeled nanoparticles; biotinylated nanoparticles, and non-biotinylated manganese(III)-labeled nanoparticles.

In a typical procedure, whole porcine blood was obtained fresh and anticoagulated (9:1, vol/vol) with sterile sodium citrate. Plasma clots were produced by combining plasma and 100 mmol/L calcium chloride (3:1 vol/vol) with 5 U thrombin (SigmaAldrich, Inc.) in a plastic tube through which a 5-0 suture was passed to provide a clotting surface (FIG. 14). The plasma was allowed to coagulate slowly at room temperature. The clots were incubated individually with 150 g biotinylated antifibrin monoclonal antibody (NIB 1H10)19 20 in 10 mL PBS with 1% crystalline BSA (Sigma Chemical Co) for 2 hours. The antibody-treated clots were then incubated with excess avidin (50 g/mL PBS) for 30 minutes, followed by biotinylated nanoparticles (30 L/mL PBS) for 30 minutes. The control clots were treated similarly with control nanoparticles (30 L/mL PBS).

Results

Figure 15:
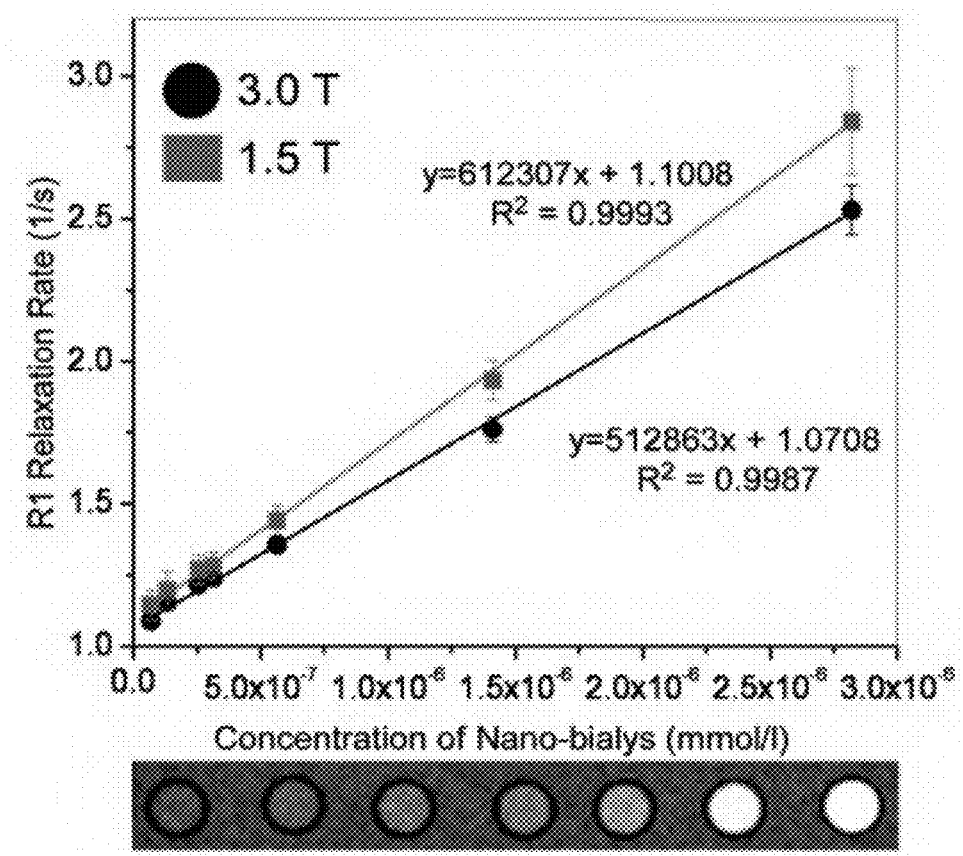
FIG. 15 depicts MRI results in suspension: longitudinal particulate r1 relaxivity. (Top) The measured R1 relaxation rate at 3.0 T (circles) and 1.5 T (squares) as a function of nanoparticles concentration. (Bottom) A T1-weighted spin echo MR image (1.5 T) showing cross-sections of test tubes showing a bright signal from the high concentration (right) with progressively lower signal with dilution.

A single slice inversion recovery sequence (i.e., the Look-Locker technique) was used to calculate the ionic (per metal) and particulate (per particle) r1 relaxivities of serially diluted nanoparticles at 1.5 T and 25° C. (FIG. 15). The ionic r1 and r2 relaxivities of Mn(III)-labeled nanoparticles were 3.7+/−1.1 $(s \cdot mmol [Mn])^{-1}$ and 5.2+/−1.1 $(s \cdot mmol [Mn])^{-1}$, respectively, and the particulate relaxivities were 612 307+/−7213 $(s \cdot mmol [nanoparticle])^{-1}$ and 866 989+/−10704 $(s \cdot mmol [nanoparticle])^{-1}$, respectively.

Figure 16:
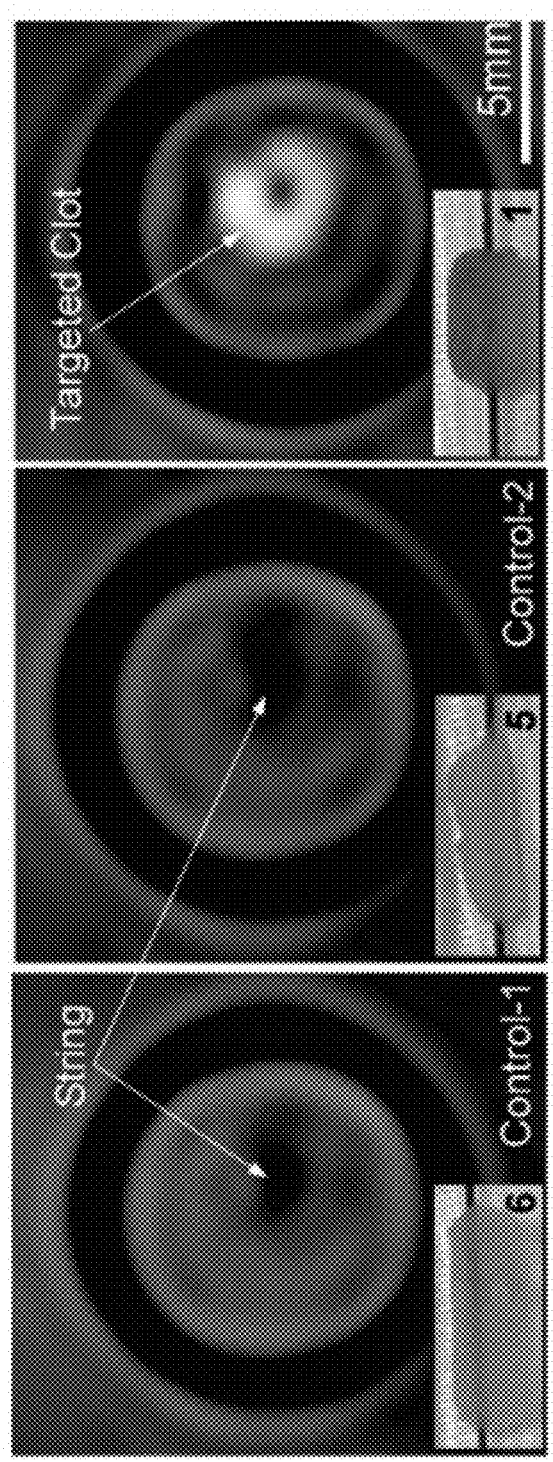
FIG. 16 depicts MRI images of fibrin-targeted manganese (III)-labeled biotinylated (right), control biotinylated nanoparticles (left), or control manganese(III)-labeled nanoparticles (center) bound to cylindrical plasma clots measured at 3.0 T. The ionic and particulate r1 relaxivities of serially diluted nanoparticles at 3.0 T were 3.1+/−1.1 (s·mmol [Mn])$^{-1}$ and 512 863+/−8408 (s·mmol [nanoparticle])$^{-1}$, respectively.

The concept of MR molecular imaging of fibrin, a critical component of intravascular thromboses, was studied in vitro. Fibrin-rich clots supported on silk suture were suspended in phosphate buffered saline (PBS, pH 7.4) with sealed polystyrene test tubes (75 mm). Nanoparticles with biotin and metal, with biotin and no metal, or no biotin with metal were targeted to the fibrin clots with classic avidin-biotin interactions and well-characterized biotinylated fibrin-specific monoclonal antibodies. Magnetic resonance images (3 T) of the clots were acquired using T1-weighted gradient echo images and a birdcage coil oriented with all groups visible within the imaging slice. MR images of clot samples (FIG. 16) showed marked contrast enhancement of the fibrin-targeted Mn(III) nanoparticles and no contrast improvement from the nontargeted and metal-free nanoparticles.

Example 11

Drug Delivery by Nanoparticles

One of two approaches may be used to incorporate drugs into the nanoparticles. In the first approach, hydrophilic drugs are mixed with a pre-formed aqueous suspension of the nanoparticle, followed by a brief shaking/swirling. In the second approach, both water soluble and insoluble drugs can be premixed with the amphiphilic polymer before the self-assembly and sonication procedure. The potential of nanoparticles for drug delivery applications was assessed with two candidate chemotherapeutic agents, hydrophilic (e.g., doxorubicin) and hydrophobic (e.g., camptothecin) in vitro.

General Protocol for Encapsulating Hydrophilic and Soluble Drugs

Amphiphilic polymer (~30 mg) was taken up in 3 mL of anhydrous chloroform (Aldrich, Inc.) and gently vortexed for 2 min. The organic phase (with or without the presence of any contrast agent, ~5 mL of chloroform layer) was dried (anhydrous $Na_2SO_4$). Excess of anhydrous chloroform (35 mL) was added to the organic phase and was taken in a 50 mL, long necked test tube. Doxorubicin (0.27 mg/mL) was dissolved in 5 mL of nanopure water (0.2 µM) and was injected followed by gentle vortexing for few minutes. The chloroform was then slowly evaporated under reduced pressure at 45° C. for 3045 min, maintaining the pressure at 420-440 mbar. To this, an additional 5 mL of nanopure water (0.2 µM) was injected. The dispersion was sonicated in a Branson ultra sonic bath for ½ h (until a clear dispersion formed) maintaining the bath temperature at 50° C.

General Protocol for Encapsulating Hydrophobic and Insoluble Drugs

Amphiphilic polymer (~27 mg) was taken up in 3 mL of anhydrous chloroform (Aldrich, Inc.) and gently vortexed for 2 min. The organic phase (with or without the presence of any contrast agent) was dried (anhydrous $Na_2SO_4$). Camptothecin (0.27 mg/mL) was dissolved in 2 mL of anhydrous chloroform and was injected into the solution followed by gentle vortexing for few minutes. Excess of anhydrous chloroform (35 mL) was added to the organic phase and was taken in a 50 mL, long necked test tube. To this, 5 mL of nanopure water (0.2 µM) was injected and gently vortexed for a few minutes. The chloroform was then slowly evaporated under reduced pressure at 45° C. for 30-45 min, maintaining the pressure at 420-440 mbar. To this, an additional 5 ml of nanopure water (0.2 µM) was injected. The dispersion was sonicated in a Branson ultra sonic bath for ½ h (until a clear dispersion formed) maintaining the bath temperature at 50° C.

Doxorubicin Analysis

Doxorubicin was analyzed by reversed-phase HPLC system with Waters 600S as a controller, Waters 626 pump to deliver mobile phase, Waters 717 auto sampler for injection and Waters 474 scanning fluorescence detector at wavelength ex 470 nm/em 555 nm for detection. A Vydac 218 MR54 C18 Multi-ring 4.6×250 mm S/N E961225-9-2 reversed-phase column with a mobile phase consisting of 10 mM Phosphate buffer pH 2.96; 35 vol %; methanol 65 vol % was used. The flow rate was 0.5 mL/min at ambient temperature.

In a typical procedure, 0.27 mg doxorubicin/ml (4.66E-07 mol/mL of nanoparticles solution) incubated at ambient temperature for 2 h. The mobile phase was prepared as follows. To 150 mL water added 340 µL H3PO4 85% adjust to 2.96 with saturated KOH, added water up to 175 mL then added 325 ml of methanol, filtered with Nylon membrane filters (47 mm 0.2 µm NylafloR from GelmanSciences). Doxorubicin was previously dissolved in deionized water at 1 mg/ml and stored in small aliquots in the freezer. These aliquots were used to prepare the doxorubicin standards. 1 mg/mL doxorubicin solution, 10 µl was added into 990 µl mobile phase and the final concentration was made 10 µg/mL. The solution was filtered through 0.45 µm cellulose acetate filter into an injection vial with a 1 mL plastic syringe followed by 0.2 ml, 0.1 mL, 0.05 mL, 0.025 mL injection.

250 µL of sample was taken and mixed with 250 µL Cleanascite, then incubated at room temperature for 15 min followed by centrifugation at 4000 rpm for 30 min. About 250 µL of the supernatant was taken out and injected for HPLC analysis. The amount of drug released was determined after 24 h, 48 h and 72 h of dialysis.

Results

Nanoparticles encapsulating drug were dialyzed in 60000 molecular weight cutoff dialysis tubing against an infinite sink of 0.9% NaCl, 0.2 mg/ml human serum albumin, and 0.05% sodium azide at 37° C., which was sampled and replaced daily. The loading efficiencies of doxorubicin and camptothecin were 98+/−0.1% and 99+/−0.1%, respectively, by reverse phase HPLC. Drug release over 3 days was 12+/−0.6% for doxorubicin and 20+/−3.5% for camptothecin (Table 2 and FIG. 17).

TABLE 2

Drug release profiles.

| Sample | Day | % Drug remaining |
|---|---|---|
| Doxorubicin | 1 | 93.96263556 |
| Doxorubicin | 2 | 90.54795347 |
| Doxorubicin | 3 | 87.81185818 |
| Camptothecin | 1 | 93.47588148 |
| Camptothecin | 2 | 87.57017959 |
| Camptothecin | 3 | 83.37743133 |

What is claimed is:

1. A substantially bi-concaved disc shaped nanoparticle, the nanoparticle comprising an aqueous inner core and an outer shell, wherein the outer shell comprises an amphiphilic polymer that forms a bi-layer and at least one molecule conjugated within the hydrophilic region of the amphiphilic polymer; wherein (a) the at least one molecule conjugated within the hydrophilic region of the amphiphilic polymer is selected from the group consisting of a targeting moiety, a biologically active agent, an imaging agent, and a metal atom, and (b) the amphiphilic polymer is polyethyleneimine conjugated to an amphiphilic lipid selected from palmitic acid, 10,12-pentacosadiynoic acid, and linoleic acid, such that at least 40% of free reactive groups of the polyethyleneimine are conjugated to the amphiphilic lipid.

2. The nanoparticle of claim 1, wherein the amphiphilic polymer is from about 1% to about 10% by weight of the nanoparticle.

3. The nanoparticle of claim 1, wherein the amphiphilic polymer comprising the outer shell is cross-linked by a method selected from the group consisting of a chemical means and a photo-chemical means.

4. The nanoparticle of claim 3, wherein at least 50% by weight of the available reactive groups of the amphiphilic polymer are cross-linked.

5. The nanoparticle of claim 1, wherein the surface of the amphiphilic polymer comprising the outer shell is derivatized with PEG.

6. The nanoparticle of claim 1, wherein average diameter of the nanoparticle is from about 50 nm to about 500 nm.

7. The nanoparticle of claim 1, wherein the average diameter of the nanoparticle is from about 100 nm to about 250 nm.

8. The nanoparticle of claim 1, wherein the average height of the nanoparticle is from about 30 nm to about 80 nm.

9. The nanoparticle of claim 1, wherein the nanoparticle comprises a through-hole.

10. The nanoparticle of claim 1, wherein the nanoparticle comprises a depression.

11. The nanoparticle of claim 1, wherein in the biologically active agent is a therapeutic agent selected from the group consisting of camptothecin, doxorubicin, fumagillin, and methotrexate.

12. The nanoparticle of claim 1, wherein in the imaging agent is selected from the group consisting of a contrast agent, a radionuclide, and a fluorescent molecule.

13. The nanoparticle of claim 1, wherein in the metal atom selected from the group consisting of manganese, cobalt, iron, gadolinium, copper, gold, titanium, tantalum, and iodine.

14. The nanoparticle of claim 1, wherein the nanoparticle further comprises a water soluble molecule that is contained within the aqueous inner core.

15. The nanoparticle of claim 1, wherein the nanoparticle further comprises a molecule conjugated to the surface of the outer shell of the nanoparticle.

16. The nanoparticle of claim 1, wherein the nanoparticle further comprises a molecule conjugated within the hydrophobic region of the amphiphilic polymer comprising the outer shell of the nanoparticle.

17. The nanoparticle of claim 1, wherein at least 50% of free reactive groups of the polyethyleneimine are conjugated to the amphiphilic lipid.

18. The nanoparticle of claim 1, wherein about 50% to about 60% of free reactive groups of the polyethyleneimine are conjugated to the amphiphilic lipid.

19. The nanoparticle of claim 1, wherein at least 55% of free reactive groups of the polyethyleneimine are conjugated to the amphiphilic lipid.

20. A substantially bi-concaved shaped nanoparticle comprising an aqueous inner core and a hydrophilic outer shell, wherein the outer shell comprises an amphiphilic polymer that forms a bi-layer, and wherein the nanoparticle is prepared by a process comprising the steps of:
   (a) providing the amphiphilic polymer, wherein the amphiphilic polymer comprises polyethyleneimine conjugated to an amphiphilic lipid, wherein at least 40% of the free reactive groups of the polyethyleneimine are conjugated to the amphiphilic lipid, and the amphiphilic lipid is selected from palmitic acid, linoleic acid, and 10,12-pentacosadiynoic acid;
   (b) forming a plurality of inverted micelles by agitating the amphiphilic polymer in a non-polar solvent;
   (c) mixing the product of step (b) with at least one molecule suspended in an aqueous medium until the at least one molecule is transferred from the aqueous phase to the organic phase and then separating the organic phase from the aqueous phase, wherein the at least one molecule is selected from the group consisting of a targeting moiety, a biologically active agent, an imaging agent, and a metal atom;
   (d) mixing a polar solvent with the separated organic phase from step (c), and evaporating the non-polar solvent that was in the organic phase at a pressure of about 350 mbar to 1000 mbar, such that an inversion of the inverted micelles occurs; and
   (e) agitating the product of step (d) while maintaining a temperature from about 30° C. to about 65° C. to produce a bi-concaved shaped nanoparticle that has an outer shell, wherein the outer shell comprises a bi-layer formed by the amphiphilic polymer.

* * * * *

UNITED STATES PATENT AND TRADEMARK OFFICE
CERTIFICATE OF CORRECTION

PATENT NO. : 9,468,607 B2
APPLICATION NO. : 12/682098
DATED : October 18, 2016
INVENTOR(S) : Gregory M. Lanza et al.

It is certified that error appears in the above-identified patent and that said Letters Patent is hereby corrected as shown below:

In the Specification

Column 1, Lines 7–9 delete:
"in part with Government support under Grant Number 5 U54 CA119342 awarded by NCI SCCNE"
and replace with -- with government support under HL073646 awarded by the National Institutes of Health --.

Signed and Sealed this
Fifth Day of May, 2020

Andrei Iancu
*Director of the United States Patent and Trademark Office*